United States Patent
D'Agostino et al.

(10) Patent No.: US 9,801,903 B2
(45) Date of Patent: Oct. 31, 2017

(54) TARGETING CANCER WITH METABOLIC THERAPY AND HYPERBARIC OXYGEN

(71) Applicants: Dominic Paul D'Agostino, Tampa, FL (US); Angela Marie Poff, Tampa, FL (US); Patrick Arnold, Champaign, IL (US)

(72) Inventors: Dominic Paul D'Agostino, Tampa, FL (US); Angela Marie Poff, Tampa, FL (US); Patrick Arnold, Champaign, IL (US)

(73) Assignee: University of South Florida, Tampa, FL (US)

(*) Notice: Subject to any disclaimer, the term of this patent is extended or adjusted under 35 U.S.C. 154(b) by 28 days.

(21) Appl. No.: 14/698,136

(22) Filed: Apr. 28, 2015

(65) Prior Publication Data

US 2015/0231172 A1 Aug. 20, 2015

Related U.S. Application Data

(63) Continuation of application No. PCT/US2013/072333, filed on Nov. 27, 2013.

(60) Provisional application No. 61/730,813, filed on Nov. 28, 2012.

(51) Int. Cl.
*A61K 33/00* (2006.01)
*A61K 31/225* (2006.01)
*A61K 31/047* (2006.01)

(52) U.S. Cl.
CPC ............ *A61K 33/00* (2013.01); *A61K 31/047* (2013.01); *A61K 31/225* (2013.01)

(58) Field of Classification Search
None
See application file for complete search history.

(56) References Cited

FOREIGN PATENT DOCUMENTS

WO 2012154837 A2 11/2012

OTHER PUBLICATIONS

Isidoro et al., "Alteration of the bioenergetics phenotype of mitochondria is a hallmark of breast, gastric, lung and oesophageal cancer", Biochem J 378: 17-20 (2004) (of record).*
Skinner et al., "Ketone bodies inhibit the viability of human neuroblastoma cells", J Pediatric Surg 44: 212-216 (2009) (of record).*
Zhou et al., "The calorically restricted ketogenic diet, an effective alternative therapy for malignant brain cancer", Nutrition and Metabolism 4: 1-15 (2007) (herein, Zhou) (of record).*
Fearon et al., "Cancer cachexia: influence of systemic ketosis on substrate levels and nitrogen metabolism", Am J Clin Nutr 47: 42-48 (1988) (herein, Fearon) (of record).*
Daruwalla et al., World J Surg 30: 2112-2131 (2006) (herein, Daruwalla) (of record).*
Ciraolo et al., "Model of extreme hypoglycemia in dogs made ketotic with (R,S)-1,3-butanediol acetoacetate esters", Am J Physiol 269 (Endocrinol Metab 32): E67-E75 (1995) (herein, Ciraolo) (of record).*
Gillies et al., "Causes and consequences of increased glucose metabolism of cancers", J Nucl Med 49 Suppl 2: 24S-42S (2008).*
Fife et al., "Movers and shakers: cell cytoskeleton in cancer metastasis", Br J Pharmacol 171: 5507-55023 (2014).*
Tisdale & Brennan (1983) Loss of acetoacetate coenzyme A transferase activity in tumours of peripheral tissues. British journal of cancer 47: 293-297.
Thompson, et al. (2004) Effect of dietary energy restriction on vascular density during mammary carcinogenesis. Cancer research 64: 5643-5650.
Thompson, et al. (2003) Dietary energy restriction in breast cancer prevention. Journal of mammary gland biology and neoplasia 8: 133-142.
Thompson, et al. (2004) Identification of the apoptosis activation cascade induced in mammary carcinomas by energy restriction. Cancer research 64: 1541-1545.
Vaupel & Harrison (2004) Tumor hypoxia: causative factors, compensatory mechanisms, and cellular response. The oncologist 9 Suppl 5: 4-9.
Vaupel, et al. (2004) Tumor hypoxia and malignant progression. Methods in enzymology 381: 335-354.
Vaupel, et al. (2001) Treatment resistance of solid tumors: role of hypoxia and anemia. Medical oncology (Northwood, London, England) 18: 243-259.
Warburg (1956) On respiratory impairment in cancer cells. Science 124: 269-270.
Warburg (1956) On the origin of cancer cells. Science 123: 309-314.
Wheatley, et al. (2008) Low-carbohydrate diet versus caloric restriction: effects on weight loss, hormones, and colon tumor growth in obese mice. Nutrition and cancer 60: 61-68.
Wu, et al. (2007) Multiparameter metabolic analysis reveals a close link between attenuated mitochondrial bioenergetic function and enhanced glycolysis dependency in human tumor cells. American journal of physiology Cell physiology 292: C125-136.
Zhou, et al. (2007) The calorically restricted ketogenic diet, an effective alternative therapy for malignant brain cancer. Nutrition & metabolism 4: 5.
Zhu, et al. (2005) Effects of dietary energy repletion and IGF-1 infusion on the inhibition of mammary carcinogenesis by dietary energy restriction. Molecular carcinogenesis 42: 170-176.

(Continued)

Primary Examiner — Robert A Wax
Assistant Examiner — Thor Nielsen
(74) Attorney, Agent, or Firm — Nilay J. Choksi; Robert J. Varkonyi; Smith & Hopen. P.A.

(57) ABSTRACT

A method of treating cancer using ketogenic diet, while concurrently subjecting the patient to a hyperbaric, oxygen-enriched environment. Optionally, the hyperbaric, oxygen-enriched environment is 100% oxygen at 2.5 ATA absolute. The treatment may further include administering at least 10% ketone supplementation, such as acetoacetate, adenosine monophosphate kinase, 1,3-butanediol, or ketone ester, to the patient.

6 Claims, 14 Drawing Sheets

(56) References Cited

OTHER PUBLICATIONS

Zuccoli, et al. (2010) Metabolic management of glioblastoma multiforme using standard therapy together with a restricted ketogenic diet: Case Report. Nutrition & metabolism 7: 33.

Chavko, Mikulas et al. Relationship between protein nitration and oxidation and development of hyperoxic seizures. Nitric Oxide 9 (2003) 18-23.

Ciraolo, Susan T. et al. Model of extreme hypoglycemia in dogs made ketotic with (R,S)-1,3-butanediol acetoacetate esters. American Journal of Physiology Endocrinology and Metabolism, 1995. vol. 269, pp. E67-E75.

Kim, Do Young et al. Ketones prevent synaptic dysfunction induced by mitochondrial respiratory complex inhibitors. Journal of Neurochemistry, 2010. vol. 114, pp. 130-141.

Puchowicz, Michelle A. et al. Dog model of therapeutic ketosis induced by oral administration of R,S-1,3-butanediol diacetoacetate. J. Nutr. Biochem. 11:281-287, 2000.

Restriction/election requirement issued by the U.S. Patent Office dated Jul. 3, 2014 for U.S. Appl. No. 14/078,066.

Non-final office action issued by the U.S. Patent Office dated Dec. 22, 2014 for U.S. Appl. No. 14/078,066.

International Search Report and Written Opinion issued by the International Searching Authority dated Jan. 2, 2013 for international patent application No. PCT/US2012/037099.

International Preliminary Report on Patentability issued by the International Bureau dated Nov. 21, 2013 for international patent application No. PCT/US2012/037099.

Arismendi-Morillo & Castellano-Ramirez (2008) Ultrastructural mitochondrial pathology in human astrocytic tumors: potentials implications pro-therapeutics strategies. Journal of electron microscopy 57: 33-42.

Aykin-Burns, et al. (2009) Increased levels of superoxide and H2O2 mediate the differential susceptibility of cancer cells versus normal cells to glucose deprivation. The Biochemical journal 418: 29-66.

Bennett, et al. (2008) Hyperbaric oxygenation for tumour sensitisation to radiotherapy: a systematic review of randomised controlled trials. Cancer treatment reviews 34: 577-591.

Cuezva, et al. (2002) The bioenergetic signature of cancer: a marker of tumor progression. Cancer research 62: 6674-6681.

D'Agostino, et al. (2009) Acute hyperoxia increases lipid peroxidation and induces plasma membrane blebbing in human U87 glioblastoma cells. Neuroscience 159: 1011-1033.

D'Agostino et al., Therapeutic ketosis with ketone ester delays central nervous system oxygen toxicity seizures in rats. Am J Physiol Regul Integr Comp Physiol 2013, 304(10):R829-836.

Daruwalla & Christophi (2006) Hyperbaric oxygen therapy for malignancy: a review. World journal of surgery 30: 2112-2143.

Desrochers, et al. (1995) Metabolism of (R,S)-1,3-butanediol acetoacetate esters, potential parenteral and enteral nutrients in conscious pigs. The American journal of physiology 268: E660-667.

Dhup, et al. (2012) Multiple biological activities of lactic acid in cancer: influences on tumor growth, angiogenesis and metastasis. Current pharmaceutical design 18: 1319-1330.

Duranti, et al. (2012) PET scan contribution in chest tumor management: a systematic review for thoracic surgeons. Tumori 98: 175-184.

Fearon, et al. (1988) Cancer cachexia: influence of systemic ketosis on substrate levels and nitrogen metabolism. The American journal of clinical nutrition 47: 42-48.

Hoogsteen, et al. (2007) The hypoxic tumour microenvironment, patient selection and hypoxia-modifying treatments. Clinical oncology (Royal College of Radiologists (Great Britain)) 19: 385-396.

Hursting, et al. (2010) Calories and carcinogenesis: lessons learned from 30 years of calorie restriction research. Carcinogenesis 31: 83-89.

Isidoro, et al. (2004) Alteration of the bioenergetic phenotype of mitochondria is a hallmark of breast, gastric, lung and oesophageal cancer. The Biochemical journal 378: 17-20.

John (2001) Dysfunctional mitochondria, not oxygen insufficiency, cause cancer cells to produce inordinate amounts of lactic acid: the impact of this on the treatment of cancer. Medical hypotheses 57: 429-460.

Kataoka, et al. (1991) Ultrastructural study of mitochondria in oncocytes. Ultrastructural pathology 15: 231-239.

Kies, et al. (1973) Utilization of 1,3-butanediol and nonspecific nitrogen in human adults. The Journal of nutrition 103: 1155-1163.

Kiebish, et al.(2008) Cardiolipin and electron transport chain abnormalities in mouse brain tumor mitochondria: lipidomic evidence supporting the Warburg theory of cancer. Journal of lipid research 49: 2545-2601.

Lee, et al. (2012) Starvation, detoxification, and multidrug resistance in cancer therapy. Drug resistance updates : reviews and commentaries in antimicrobial and anticancer chemotherapy 15: 114-122.

Liu & Feng (2012) PTEN, energy metabolism and tumor suppression. Acta biochimica et biophysica sinica. 44 (8):629-631.

Lunt SY, Vander Heiden MG (2011) Aerobic glycolysis: meeting the metabolic requirements of cell proliferation. Annual review of cell and developmental biology 27: 441-464.

Maalouf, et al. (2007) Ketones inhibit mitochondrial production of reactive oxygen species production following glutamate excitotoxicity by increasing NADH oxidation. Neuroscience 145: 256-264.

Magee, et al. (1979) The inhibition of malignant cell growth by ketone bodies. The Australian journal of experimental biology and medical science 57: 529-539.

Masko, et al. (2010) Low-carbohydrate diets and prostate cancer: how low is "low enough"? Cancer prevention research (Philadelphia, Pa) 3: 1124-1131.

Maurer, et al. (2011) Differential utilization of ketone bodies by neurons and glioma cell lines: a rationale for ketogenic diet as experimental glioma therapy. BMC Cancer. Jul. 26, 2011;11:315.

Mavropoulos, et al. (2006) Is there a role for a low-carbohydrate ketogenic diet in the management of prostate cancer? Urology 68: 15-18.

Mavropoulos, et al. (2009) the effects of varying dietary carbohydrate and fat content on survival in a murine LNCaP prostate cancer xenograft model. Cancer prevention research (Philadelphia, Pa) 2: 557-565.

Medina (2001) Glutamine and cancer. The Journal of nutrition 131: 2539S-2542S; discussion 2550S-2531S.

Miceli & Jazwinski (2005) Common and cell type-specific responses of human cells to mitochondrial dysfunction. Experimental Cell Research 302: 270-280.

Modica-Napolitano & Singh (2004) Mitochondrial dysfunction in cancer. Mitochondrion 4: 755-817.

Moen, et al. (2009) Hyperoxic treatment induces mesenchymal-to-epithelial transition in a rat adenocarcinoma model. PloS one. 4(7):e6381.

Moen & Stuhr (2012) Hyperbaric oxygen therapy and cancer-a review. Targeted oncology. 7(4):233-42.

Mukherjee, et al. (2002) Dietary restriction reduces angiogenesis and growth in an orthotopic mouse brain tumour model. British journal of cancer 86: 1615-1621.

Mukherjee, et al. (2008) Differential effects of energy stress on AMPK phosphorylation and apoptosis in experimental brain tumor and normal brain. Molecular cancer 7: 37.

Mukherjee, et al. (1999) Energy intake and prostate tumor growth, angiogenesis, and vascular endothelial growth factor expression. Journal of the National Cancer Institute 91: 512-523.

Nebeling & Lerner (1995) Implementing a ketogenic diet based on medium-chain triglyceride oil in pediatric patients with cancer. Journal of the American Dietetic Association 95: 693-697.

Otto, et al. (2008) Growth of human gastric cancer cells in nude mice is delayed by a ketogenic diet supplemented with omega-3 fatty acids and medium-chain triglycerides. BMC cancer 8: 122.

Oudard, et al. (1997) Gliomas are driven by glycolysis: putative roles of hexokinase, oxidative phosphorylation and mitochondrial ultrastructure. Anticancer research 17: 1903-1911.

(56) References Cited

OTHER PUBLICATIONS

Petre, et al. (2003) Hyperbaric oxygen as a chemotherapy adjuvant in the treatment of metastatic lung tumors in a rat model. The Journal of thoracic and cardiovascular surgery 125: 85.
Puchowicz, et al. (2000) Dog model of therapeutic ketosis induced by oral administration of R,S-1,3-butanediol diacetoacetate. The Journal of nutritional biochemistry 11: 281-287.
Rossifanelli, et al. (1991) Effect of Energy Substrate Manipulation on Tumor-Cell Proliferation in Parenterally Fed Cancer-Patients. Clinical Nutrition 10: 228-232.
Sawai, et al. (2004) Growth-inhibitory effects of the ketone body, monoacetoacetin, on human gastric cancer cells with succinyl-CoA: 3-oxoacid CoA-transferase (SCOT) deficiency. Anticancer research 24: 2213-2217.
Schumacker (2006) Reactive oxygen species in cancer cells: live by the sword, die by the sword. Cancer cell 10: 175-181.
Seyfried, et al. (2008) Targeting energy metabolism in brain cancer with calorically restricted ketogenic diets. Epilepsia 49 Suppl 8: 114-116.
Seyfried & Shelton (2010) Cancer as a metabolic disease. Nutrition & metabolism 7: 7.
Seyfried, et al. (2003) Role of glucose and ketone bodies in the metabolic control of experimental brain cancer. British journal of cancer 89: 1375-1457.
Skinner, et al. (2009) Ketone bodies inhibit the viability of human neuroblastoma cells. Journal of pediatric surgery 44: 212.
Stuhr, et al. (2004) Hyperbaric oxygen alone or combined with 5-FU attenuates growth of DMBA-induced rat mammary tumors. Cancer letters 210: 35-75.
Takiguchi, et al. (2001) Use of 5-FU plus hyperbaric oxygen for treating malignant tumors: evaluation of antitumor effect and measurement of 5-FU in individual organs. Cancer chemotherapy and pharmacology 47: 11-14.
Tisdale & Brennan; A comparison of long-chain triglycerides and medium-chain triglycerides on weight loss and tumor size in a cachexia model. British jounral of cancer. 1988; 58(5):580-3.

Partial Supplementary European Search Report (Form 1507US) dated Jun. 8, 2016 for corresponding European Application No. 13857810.9.
Extended European Search Report (Form 1507S) dated Sep. 13, 2016 for corresponding European Application No. 13857810.9.
Poff, Angela M., et al. Supplemental ketone metabolic therapy slows tumor growth and increases survival time in mice with metastatic cancer. The FASEB Journal, vol. 27, No. 1, Apr. 2013. Abstract.
Kossoff et al., The Ketogenic and Modified Atkins Diets, Springer Publishing Company, 2016, pp. 1-4.
Fife et al., Movers and shakers: cell cytoskeleton in cancer metastasis, British Journal of Pharmacology, 2014, vol. 171, pp. 5507-5523.
Fine et al., Acetoacetate reduces growth and ATP concentration in cancer cell lines which over-express uncoupling protein 2, Cancer Cell International, 2009, vol. 9:14.
Gillies et al., Causes and Consequences of Increased Glucose Metabolism of Cancers, The Journal of Nuclear Medicine, vol. 49, No. 6 (Suppl), Jun. 2008.
Kesl et al., Effects of exogenous ketone supplementation on blood ketone, glucose, triglyceride, and lipoprotein levels in Sprague—Dawley rats, Nutrition & Metabolism (2016) 13:9.
McDonald, The Ketogenic Diet, A complete guide for the Dieter and Practitioner, 1998, Sixth edition, pp. 1-5.
Liberti et al., The Warburg Effect: How Does it Benefit Cancer Cells?, Trends in Biochemical Sciences, Mar. 2016, vol. 41, No. 3, pp. 211-218.
Ye, et al., Efficacy of and patient compliance with a ketogenic diet in adults with intractable epilepsy: a meta-analysis. J Clin Neurol. Jan. 2015;11(1):26-31.
D'Agostino, et al., Therapeutic ketosis with ketone ester delays central nervous system oxygen toxicity seizures in rats. Am J Physiol Regul Integr Comp Physiol. May 15, 2013;304(10):R829-36.
http://www.mayomedicallaboratories.com/test-catalog/Clinical+and+Interpretive/9251, last accessed Mar. 13, 2017.

\* cited by examiner

TARGETING CANCER WITH METABOLIC THERAPY AND HYPERBARIC OXYGEN

CROSS-REFERENCE TO RELATED APPLICATIONS

This application is a continuation of prior filed International Application No. PCT/US2013/072333, filed Nov. 27, 2013, which claims priority to U.S. Provisional Application No. 61/730,813 entitled: "Targeting Cancer with Metabolic Therapy and Hyperbaric Oxygen," filed Nov. 28, 2012, the contents of which are hereby incorporated by reference.

FIELD OF THE INVENTION

This invention relates to methods of treating cancers and oncogenic diseases. Specifically, the invention provides a novel method of targeting cancerous tissues using hyperbaric oxygen and ketone-based metabolic therapy.

BACKGROUND OF THE INVENTION

Despite decades of intensive research, cancer remains the second leading cause of death in the United States. One in every two men and one in three women will develop cancer in their lifetime, with one in four men and one in five women dying from cancer. Though cancer has shown a slow decline since early 1990's, in part due to early detection, preventative measures, decreased tobacco use, advances in the field have done little to improve the survival outcome of patients with late-stage metastatic cancer. Standard care typically involves surgery, chemotherapy, and radiation, but these treatments often cause toxic side effects and may even promote cancer progression and metastasis (Sun, et al. (2012) Treatment-induced damage to the tumor microenvironment promotes prostate cancer therapy resistance through WNT16B. Nature medicine; Seyfried, et al. (2010) Does the existing standard of care increase glioblastoma energy metabolism? The lancet oncology 11: 811-813). While many primary tumors can be controlled with conventional therapies, these treatments are largely ineffective against long-term management of metastatic disease (Graeme, et al. (2004) The contribution of cytotoxic chemotherapy to 5-year survival in adult malignancies. Clinical Oncology 16).

Metastasis is a complex phenomenon in which cancer cells spread from a primary tumor to establish foci in a distal tissue. The specific changes which mediate metastasis remain unclear; however, the process generally involves local tumor growth, invasion through the basement membrane and surrounding tissue, intravasation into the blood vessels, dissemination and survival in circulation, extravasation from the vasculature, and re-establishment of tumors at distal tissues. As metastasis is responsible for over 90 percent of cancer-related deaths, there is a substantial need for novel treatments effective against metastatic cancer (Gupta & Massagué (2006) Cancer metastasis: building a framework. Cell 127: 679-695). While many primary tumors can be controlled with conventional therapies like surgery, chemotherapy, and radiation, these treatments are often ineffective against long-term management of metastatic disease which is responsible for 90 percent of cancer-related deaths (Graeme, et al. (2004) The contribution of cytotoxic chemotherapy to 5-year survival in adult malignancies. Clinical Oncology 16; Gupta & Massagué (2006) Cancer metastasis: building a framework. Cell 127: 679-695). There is a substantial need for novel treatments effective against metastatic cancer. The epithelial-to-mesenchymal transition (EMT) is the activation of a latent embryonic program causing a switch from epithelial to mesenchymal phenotype, and alterations in cell-cell/cell-matrix, which enhances cellular motility. Key cellular processes involved in EMT in vitro have been shown to affect metastatic spread in vivo, though metastasis is difficult to study in vivo due to the lack of adequate animal models.

Eighty-eight percent of ATP is made via oxidative phosphorylation in the mitochondria, through an oxygen-dependent pathway. Hypoxic conditions cause a shift to anaerobic fermentation, whereby ATP is produced through substrate level phosphorylation in an oxygen independent pathway. This adaptation to hypoxic mediated fermentation, which is an inefficient process for a rapidly dividing cell, requires HIF-1.

While the major oncogene and tumor suppressor gene mutations can be found in many different cancers, one of the only universal traits of tumor cells across tissue types is abnormal energy metabolism (Seyfried & Shelton (2010) Cancer as a metabolic disease. Nutrition & metabolism 7: 7). In the 1930s, Otto Warburg observed that cancer cells express abnormal energy metabolism characterized by very high rates of aerobic glycolysis (fermentation in the presence of oxygen) (Warburg (1956) On the origin of cancer cells. Science 123: 309-314; Warburg (1956) On respiratory impairment in cancer cells. Science 124: 269-270). This feature, known as The Warburg Effect, is a consequence of mitochondrial dysfunction and genetic mutations within the cancer cell (Seyfried & Shelton (2010) Cancer as a metabolic disease. Nutrition & metabolism 7: 7). While healthy cells derive the vast majority of their energy from ATP production by oxidative phosphorylation (OXPHOS) in the mitochondria, cancer cells rely almost exclusively on ATP production by substrate level phosphorylation (SLP) (Seyfried & Shelton (2010) Cancer as a metabolic disease. Nutrition & metabolism 7: 7). Nearly ubiquitously, cancers utilize SLP of glycolysis in the cytoplasm, as seen in FIG. 1, and, in some cancers, of glutaminolysis and the Kreb's Cycle (Lunt S Y, Vander Heiden M G (2011) Aerobic glycolysis: meeting the metabolic requirements of cell proliferation. Annual review of cell and developmental biology 27: 441-464; Medina (2001) Glutamine and cancer. The Journal of nutrition 131: 2539S-2542S; discussion 2550S-2531S). In fact, cancer cells undergo glycolysis at a rate up to 200-times that of healthy cells (Warburg (1956) On respiratory impairment in cancer cells. Science 124: 269-270). It is well documented that cancer cells across tissue types possess an array of mitochondrial damage, including loss of mitochondrial number, mitochondrial swelling, partial or total cristolysis, abnormalities in mitochondrial lipid composition, and absent, mutated, or decreased activity of mitochondrial enzymes involved in OXPHOS (Cuezva, et al. (2002) The bioenergetic signature of cancer: a marker of tumor progression. Cancer research 62: 6674-6681; Isidoro, et al. (2004) Alteration of the bioenergetic phenotype of mitochondria is a hallmark of breast, gastric, lung and oesophageal cancer. The Biochemical journal 378: 17-20; Arismendi-Morillo & Castellano-Ramirez (2008) Ultrastructural mitochondrial pathology in human astrocytic tumors: potentials implications pro-therapeutics strategies. Journal of electron microscopy 57: 33-42; Kiebish, et al. (2008) Cardiolipin and electron transport chain abnormalities in mouse brain tumor mitochondria: lipidomic evidence supporting the Warburg theory of cancer. Journal of lipid research 49: 2545-2601; Modica-Napolitano & Singh (2004) Mitochondrial dysfunction in cancer. Mitochondrion 4: 755-817; Kataoka, et al. (1991) Ultrastructural study of mitochondria in oncocytes. Ultrastructural pathology 15: 231-239). With this severe mitochondrial damage, cancer cells are unable to produce adequate amounts of ATP through OXPHOS to maintain viability and are forced to up-regulate SLP and glycolysis to survive (Seyfried & Shelton (2010) Cancer as a metabolic disease. Nutrition & metabolism 7: 7). Many of the genes that mediate this shift are known oncogenes and tumor suppressor genes. HIF-1α, IGF-1/PI3K/Akt, MYC, mTOR, and Ras upregulate glycolytic enzymes and GLUT transporter expression (Seyfried & Shelton (2010) Cancer as a metabolic disease. Nutrition & metabolism 7: 7; Miceli & Jazwinski (2005) Common and cell type-specific responses of human cells to mitochondrial dysfunction. Experimental Cell Research 302: 270-280); p53 and PTEN inhibit these responses and are thus inhibited (Liu & Feng (2012) PTEN, energy metabolism and tumor suppression. Acta biochimica et biophysica Sinica).

This fermentative phenotype causes cancers to excrete large quantities of lactate, creating an acidic tumor microenvironment that promotes epithelial to mesenchymal transition (EMT), invasion, and metastasis (Walenta, et al. (2000) High lactate levels predict likelihood of metastases, tumor recurrence, and restricted patient survival in human cervical cancers. Cancer research 60: 916-921; Dhup, et al. (2012) Multiple biological activities of lactic acid in cancer: influences on tumor growth, angiogenesis and metastasis. Current pharmaceutical design 18: 1319-1330). Lactate can also be returned to the cancer as glucose via the Cori Cycle, replenishing fuel for the glycolysis-dependent tumor cells, as seen in FIG. 1. Due to this metabolic deficiency, cancer cells have elevated rates of glucose consumption relative to healthy cells—a quality that underlies the use of fluorodeoxyglucose-PET scans as an important diagnostic tool for oncologists (Duranti, et al. (2012) PET scan contribution in chest tumor management: a systematic review for thoracic surgeons. Tumori 98: 175-184).

The Warburg Effect creates a glucose-dependency which can be targeted therapeutically (Seyfried & Shelton (2010) Cancer as a metabolic disease. Nutrition & metabolism 7: 7; Seyfried, et al. (2008) Targeting energy metabolism in brain cancer with calorically restricted ketogenic diets. Epilepsia 49 Suppl 8: 114-116). Ketogenic diets (KDs) are high fat, low or no carbohydrate diets that have been used to treat pediatric refractory epilepsy for decades (Katyal, et al. (2000) The ketogenic diet in refractory epilepsy: the experience of Children's Hospital of Pittsburgh. Clinical pediatrics 39: 153-159). KDs naturally suppress appetite and often lead to dietary energy restriction (DER) and body weight loss (Katyal, et al. (2000) The ketogenic diet in refractory epilepsy: the experience of Children's Hospital of Pittsburgh. Clinical pediatrics 39: 153-159) or decreased lean body mass (Katyal, et al. (2000) The ketogenic diet in refractory epilepsy: the experience of Children's Hospital of Pittsburgh. Clinical pediatrics 39: 153-159; Paoli, et al. (2012) Ketogenic diet does not affect strength performance in elite artistic gymnasts. Journal of the International Society of Sports Nutrition 9: 34; Johnstone, et al. (2008) Effects of a high-protein ketogenic diet on hunger, appetite, and weight loss in obese men feeding ad libitum. The American journal of clinical nutrition 87: 44-55; Hussain, et al. (2012) Effect of low-calorie versus low-carbohydrate ketogenic diet in type 2 diabetes. Nutrition 28: 1016-1021; Volek, et al. (2004) Comparison of energy-restricted very low-carbohydrate and low-fat diets on weight loss and body composition in overweight men and women. Nutrition & metabolism 1: 13). While low carbohydrate or KDs promote weight loss in overweight individuals, they are known to spare muscle wasting during DER (Paoli, et al. (2012) Ketogenic diet does not affect strength performance in elite artistic gymnasts. Journal of the International Society of Sports Nutrition 9: 34; Manninen (2006) Very-low-carbohydrate diets and preservation of muscle mass. Nutrition & metabolism 3: 9; Cahill (2006) Fuel metabolism in starvation. Annual review of nutrition 26: 1-22; Veech (2004) The therapeutic implications of ketone bodies: the effects of ketone bodies in pathological conditions: ketosis, ketogenic diet, redox states, insulin resistance, and mitochondrial metabolism. Prostaglandins, leukotrienes, and essential fatty acids 70: 309-319). DER has been shown to slow disease progression in a variety of cancers, including brain, prostate, mammary, pancreas, lung, gastric, and colon (Seyfried & Shelton (2010) Cancer as a metabolic disease. Nutrition & metabolism 7: 7; Zuccoli, et al. (2010) Metabolic management of glioblastoma multiforme using standard therapy together with a restricted ketogenic diet: Case Report. Nutrition & metabolism 7: 33; Mavropoulos, et al. (2006) Is there a role for a low-carbohydrate ketogenic diet in the management of prostate cancer? Urology 68: 15-18; Zhou, et al. (2007) The calorically restricted ketogenic diet, an effective alternative therapy for malignant brain cancer. Nutrition & metabolism 4: 5; Mavropoulos, et al. (2009) The effects of varying dietary carbohydrate and fat content on survival in a murine LNCaP prostate cancer xenograft model. Cancer prevention research (Philadelphia, Pa.) 2: 557-565; Otto, et al. (2008) Growth of human gastric cancer cells in nude mice is delayed by a ketogenic diet supplemented with omega-3 fatty acids and medium-chain triglycerides. BMC cancer 8: 122; Masko, et al. (2010) Low-carbohydrate diets and prostate cancer: how low is "low enough"? Cancer prevention research (Philadelphia, Pa.) 3: 1124-1131; Tisdale & Brennan; A comparison of long-chain triglycerides and medium-chain triglycerides on weight loss and tumor size in a cachexia model.pdf; Wheatley, et al. (2008) Low-carbohydrate diet versus caloric restriction: effects on weight loss, hormones, and colon tumor growth in obese mice. Nutrition and cancer 60: 61-68; Rossifanelli, et al. (1991) Effect of Energy Substrate Manipulation on Tumor-Cell Proliferation in Parenterally Fed Cancer-Patients. Clinical Nutrition 10: 228-232). DER appears to facilitate its anti-cancer effects through several metabolic pathways, including inhibition of the IGF-1/PI3K/Akt signaling pathway which promotes proliferation and angiogenesis and inhibits apoptosis (Mukherjee, et al. (2002) Dietary restriction reduces angiogenesis and growth in an orthotopic mouse brain tumour model. British journal of cancer 86: 1615-1621; Mukherjee, et al. (1999) Energy intake and prostate tumor growth, angiogenesis, and vascular endothelial growth factor expression. Journal of the National Cancer Institute 91: 512-523; Thompson, et al. (2004) Effect of dietary energy restriction on vascular density during mammary carcinogenesis. Cancer research 64: 5643-5650; Hursting, et al. (2010) Calories and carcinogenesis: lessons learned from 30 years of calorie restriction research. Carcinogenesis 31: 83-89; Thompson, et al. (2003) Dietary energy restriction in breast cancer prevention. Journal of mammary gland biology and neoplasia 8: 133-142; Thompson, et al. (2004) Identification of the apoptosis activation cascade induced in mammary carcinomas by energy restriction. Cancer research 64: 1541-1545; Zhu, et al. (2005) Effects of dietary energy repletion and IGF-1 infusion on the inhibition of mammary carcinogenesis by dietary energy restriction. Molecular carcinogenesis 42: 170-176). DER has been shown to induce apoptosis in astrocytoma cells but protect normal brain cells from death through activation of adenosine monophosphate kinase (AMPK) (Mukherjee, et al. (2008) Differential effects of energy stress on AMPK phosphorylation and apoptosis in experimental brain tumor and normal brain. Molecular cancer 7: 37). The KD has been successfully used as an adjuvant therapy for Glioblastoma Multiforme (GBM) in a small number of case reports with patients exhibiting marked improvements in quality of life, dramatic slowing of tumor growth, or disappearance of tumor altogether (Zuccoli, et al. (2010) Metabolic management of glioblastoma multiforme using standard therapy together with a restricted ketogenic diet: Case Report. Nutrition & metabolism 7: 33; Nebeling & Lerner (1995) Implementing a ketogenic diet based on medium-chain triglyceride oil in pediatric patients with cancer. Journal of the American Dietetic Association 95: 693-697). Furthermore, a pilot trial of patients with advanced metastatic disease of varying tissue types reported that the KD improved emotional functioning and quality of life in terminally ill patients (Schmidt, et al. (2011) Effects of a ketogenic diet on the quality of life in 16 patients with advanced cancer: A pilot trial. Nutr Metab (Lond). 2011 Jul. 27; 8(1):54).

As such, any conditions which restrict glucose availability (or impair glycolysis) while providing alternative energy sources for healthy cells, can selectively starve cancer cells while leaving normal cells unharmed. Metabolic therapy in the forms of dietary energy restriction or the ketogenic diet (KD) have been shown to elicit anti-cancer effects in a variety of cancers, likely by restricting glucose availability to the tumor and by inhibiting oncogenes that promote cancer progression (Seyfried & Shelton (2010) Cancer as a metabolic disease. Nutrition & metabolism 7: 7; Zhou, et al. (2007) The calorically restricted ketogenic diet, an effective alternative therapy for malignant brain cancer. Nutrition & metabolism 4: 5; Zuccoli, et al. (2010) Metabolic management of glioblastoma multiforme using standard therapy together with a restricted ketogenic diet: Case Report. Nutrition & metabolism 7: 33; Mavropoulos, et al. (2006) Is there a role for a low-carbohydrate ketogenic diet in the management of prostate cancer? Urology 68: 15-18). The two most abundant and physiologically relevant ketone bodies are acetoacetate (ACA) and β-hydroxybutyrate (βHB). Ketone bodies are metabolized exclusively in the mitochondria via the Kreb's Cycle and OXPHOS coupled to the electron transport chain. These metabolic strategies elevate blood ketone concentrations. Due to mitochondrial damage, most cancers are unable to utilize ketones for energy (Maurer, et al. (2011) Differential utilization of ketone bodies by neurons and glioma cell lines: a rationale for ketogenic diet as experimental glioma therapy. BMC Cancer. 2011 Jul. 26; 11:315; Cuezva, et al. (2002) The bioenergetic signature of cancer: a marker of tumor progression. Cancer research 62: 6674-6681; Fearon, et al. (1988) Cancer cachexia: influence of systemic ketosis on substrate levels and nitrogen metabolism. The American journal of clinical nutrition 47: 42-48; Sawai, et al. (2004) Growth-inhibitory effects of the ketone body, monoacetoacetin, on human gastric cancer cells with succinyl-CoA: 3-oxoacid CoA-transferase (SCOT) deficiency. Anticancer research 24: 2213-2217; Seyfried, et al. (2003) Role of glucose and ketone bodies in the metabolic control of experimental brain cancer. British journal of cancer 89: 1375-1457; Oudard, et al. (1997) Gliomas are driven by glycolysis: putative roles of hexokinase, oxidative phosphorylation and mitochondrial ultrastructure. Anticancer research 17: 1903-1911; John (2001) Dysfunctional mitochondria, not oxygen insufficiency, cause cancer cells to produce inordinate amounts of lactic acid: the impact of this on the treatment of cancer. Medical hypotheses 57: 429-460; Wu, et al. (2007) Multiparameter metabolic analysis reveals a close link between attenuated mitochondrial bioenergetic function and enhanced glycolysis dependency in human tumor cells. American journal of physiology Cell physiology 292: C125-136; Skinner, et al. (2009) Ketone bodies inhibit the viability of human neuroblastoma cells. Journal of pediatric surgery 44: 212; Sawai, et al. (2004) Growth-inhibitory effects of the ketone body, monoacetoacetin, on human gastric cancer cells with succinyl-CoA: 3-oxoacid CoA-transferase (SCOT) deficiency. Anticancer research 24: 2213-2217; Tisdale & Brennan (1983) Loss of acetoacetate coenzyme A transferase activity in tumours of peripheral tissues. British journal of cancer 47: 293-297).

Furthermore, ketones have been shown to inhibit cancer cell proliferation (Skinner, et al. (2009) Ketone bodies inhibit the viability of human neuroblastoma cells. Journal of pediatric surgery 44: 212; Sawai, et al. (2004) Growth-inhibitory effects of the ketone body, monoacetoacetin, on human gastric cancer cells with succinyl-CoA: 3-oxoacid CoA-transferase (SCOT) deficiency. Anticancer research 24: 2213-2217; Magee, et al. (1979) The inhibition of malignant cell growth by ketone bodies. The Australian journal of experimental biology and medical science 57: 529-539). Many cancers do not express the Succinyl-CoA: 3-ketoacid CoA-Transferase (SCOT) enzyme, which is required for ketone body metabolism (Sawai, et al. (2004) Growth-inhibitory effects of the ketone body, monoacetoacetin, on human gastric cancer cells with succinyl-CoA: 3-oxoacid CoA-transferase (SCOT) deficiency. Anticancer research 24: 2213-2217; Tisdale & Brennan (1983) Loss of acetoacetate coenzyme A transferase activity in tumours of peripheral tissues. British journal of cancer 47: 293-297). βHB administration rescues healthy brain cells from glucose withdrawal-induced cell death but does not protect glioma cells (Maurer, et al. (2011) Differential utilization of ketone bodies by neurons and glioma cell lines: a rationale for ketogenic diet as experimental glioma therapy. BMC Cancer. 2011 Jul. 26; 11:315). While ketones are not an energy source for cancer cells, they are an efficient energy substrate for healthy tissue in the rest of the body. Ketones have been shown to inhibit cancer cell growth and proliferation in vitro in a variety of cell lines, including gastric cancer, transformed lymphoblasts, kidney cancer, HeLa cells, and melanoma (Magee, et al. (1979) The inhibition of malignant cell growth by ketone bodies. The Australian journal of experimental biology and medical science 57: 529-539; Sawai, et al. (2004) Growth-inhibitory effects of the ketone body, monoacetoacetin, on human gastric cancer cells with succinyl-CoA: 3-oxoacid CoA-transferase (SCOT) deficiency. Anticancer research 24: 2213-2217). It is unclear exactly how ketones elicit their anti-cancer effects. Ketone bodies are known to inhibit glycolysis, which may contribute to their efficacy (Wu & Thompson (1988) The effect of ketone bodies on alanine and glutamine metabolism in isolated skeletal muscle from the fasted chick. The Biochemical journal 255: 139-144). Additionally, ketones are transported into the cell via the monocarboxylate transporters (MCTs) which are also responsible for exporting the fermentation product lactate from the cell into the circulation. Lactate confers an acidic tumor microenvironment and is known to play a large role in invasion and metastasis (Dhup, et al. (2012) Multiple biological activities of lactic acid in cancer: influences on tumor growth, angiogenesis and metastasis. Current pharmaceutical design 18: 1319-1330). Furthermore, it has been well-documented that both calorie restriction and fasting, conditions where ketones take over as a primary fuel, possess very potent anti-cancer effects, further supporting the observation that cancer cells cannot thrive by using ketone bodies for fuel (Hursting, et al. (2010) Calories and carcinogenesis: lessons learned from 30 years of calorie restriction research. Carcinogenesis 31: 83-89; Lee, et al. (2012) Starvation, detoxification, and multidrug resistance in cancer therapy. Drug resistance updates: reviews and commentaries in antimicrobial and anticancer chemotherapy 15: 114-122).

However, the present methods only provide enhanced anticancer effects. As such, enhanced anticancer therapies are required which reduce cancer growth as well as metastasis.

SUMMARY OF THE INVENTION

The present invention provides a method of treating cancer by administering a ketogenic diet to an animal and subjecting the animal to a hyperbaric, oxygen-enriched environment. The combined therapy provides synergistic anticancer effects, as discussed below, reducing cancer cell load and limiting metastasis. The hyperbaric, oxygen-enriched environment is optionally 100% oxygen, and in some embodiments the hyperbaric, oxygen-enriched environment is at 2.5 ATA absolute. Moreover, the animal is optionally subjected to the hyperbaric, oxygen-enriched environment for 90 minutes three times a week. In normal tissues, hypoxia inhibits mitochondrial production of ATP, stimulating an up-regulation of glycolysis to meet energy needs. Thus, the cellular response to tumor hypoxia is mediated by several of the same pathways that are overly active in cancer cells with mitochondrial damage and high rates of glycolysis. This suggests that metabolic therapy and $HBO_2T$ target several overlapping pathways and behaviors of cancer cells.

Hyperbaric oxygen therapy ($HBO_2T$) is the administration of 100% oxygen at elevated pressure (greater than sea level, 1 ATA). $HBO_2T$ increases plasma oxygen saturation, facilitating oxygen delivery to the tissue independent of hemoglobin $O_2$ saturation (Gill & Bell (2004) Hyperbaric oxygen: its uses, mechanisms of action and outcomes. QJM 97). Traditional cancer treatment, such as radiation and many chemotherapy drugs, work by producing free radicals within the tumors, leading to cell death. Cancer cells with mitochondrial damage and chaotic oxygen perfusion produce chronically elevated levels of reactive oxygen species (ROS) but are susceptible to oxidative damage-induced cell death with even modest increases in ROS (Daruwalla & Christophi (2006) Hyperbaric oxygen therapy for malignancy: a review. World journal of surgery 30: 2112-2143; Aykin-Burns, et al. (2009) Increased levels of superoxide and H2O2 mediate the differential susceptibility of cancer cells versus normal cells to glucose deprivation. The Biochemical journal 418: 29-66; Schumacker (2006) Reactive oxygen species in cancer cells: live by the sword, die by the sword. Cancer cell 10: 175-181). $HBO_2T$ enhances tumor-cell production of ROS which can damage or kill cancer cells (D'Agostino, et al. (2009) Acute hyperoxia increases lipid peroxidation and induces plasma membrane blebbing in human U87 glioblastoma cells. Neuroscience 159: 1011-1033) and likely contributes to the synergistic effects of $HBO_2T$ as an adjuvant treatment to standard care (Schumacker (2006) Reactive oxygen species in cancer cells: live by the sword, die by the sword. Cancer cell 10: 175-181). Indeed, $HBO_2T$ has been demonstrated to enhance the efficacy of both radiation and chemotherapy in animal models (Stuhr, et al. (2004) Hyperbaric oxygen alone or combined with 5-FU attenuates growth of DMBA-induced rat mammary tumors. Cancer letters 210: 35-75; Bennett, et al. (2008) Hyperbaric oxygenation for tumour sensitisation to radiotherapy: a systematic review of randomised controlled trials. Cancer treatment reviews 34: 577-591; Takiguchi, et al. (2001) Use of 5-FU plus hyperbaric oxygen for treating malignant tumors: evaluation of antitumor effect and measurement of 5-FU in individual organs. Cancer chemotherapy and pharmacology 47: 11-14; Daruwalla & Christophi (2006) Hyperbaric oxygen therapy for malignancy: a review. World journal of surgery 30: 2112-2143; Moen, et al. (2009) Hyperoxic treatment induces mesenchymal-to-epithelial transition in a rat adenocarcinoma model. PloS one 4; Petre, et al. (2003) Hyperbaric oxygen as a chemotherapy adjuvant in the treatment of metastatic lung tumors in a rat model. The Journal of thoracic and cardiovascular surgery 125: 85; Moen & Stuhr (2012) Hyperbaric oxygen therapy and cancer—a review. Targeted oncology). Preclinical data suggests $HBO_2T$ is efficacious in the treatment of cancer, but additional studies are needed to support its use (Moen & Stuhr (2012) Hyperbaric oxygen therapy and cancer—a review. Targeted oncology).

The treatment optionally includes administering a ketone supplementation set to at least 10%, such as between 10% and 20%. Exemplary amounts include 10%, 11%, 12%, 13%, 14%, 15%, 16%, 17%, 18%, 19%, 20% supplementation. Ketone supplementation is optionally acetoacetate, adenosine monophosphate kinase, 1,3-butanediol, ketone ester, 1,3-butanediol acetoacetate monoester, 1,3-butanediol acetoacetate diester, MCT oil, or R,S-1,3-butanediol-diacetoacetate ester. The supplementation can be one or a combination of ketone esters, such as a combination of R,S-1,3-butanediol acetoacetate monoester and R,S-1,3-butanediol acetoacetate diester. In some embodiments, the ketone ester supplementation is administered about 30 minutes prior to subjecting the animal to the hyperbaric, oxygen-enriched environment.

Supplemental ketone administration to enhance the efficacy of ketogenic diet metabolic therapy. Tumors also possess abnormal vasculature which blocks adequate tissue perfusion, leading to the presence of hypoxic regions that confer chemotherapy and radiation resistance and activate a number of oncogene pathways that promote cancer progression (Vaupel & Harrison (2004) Tumor hypoxia: causative factors, compensatory mechanisms, and cellular response. The oncologist 9 Suppl 5: 4-9; Hoogsteen, et al. (2007) The hypoxic tumour microenvironment, patient selection and hypoxia-modifying treatments. Clinical oncology (Royal College of Radiologists (Great Britain)) 19: 385-396; Vaupel, et al. (2001) Treatment resistance of solid tumors: role of hypoxia and anemia. Medical oncology (Northwood, London, England) 18: 243-259; Vaupel, et al. (2004) Tumor hypoxia and malignant progression. Methods in enzymology 381: 335-354). Hyperbaric oxygen therapy ($HBO_2T$) increases oxygen concentration in tissues, potentially leading to a reversal of the cancer-promoting effects of tumor hypoxia (Vaupel & Harrison (2004) Tumor hypoxia: causative factors, compensatory mechanisms, and cellular response. The oncologist 9 Suppl 5: 4-9; Hoogsteen, et al. (2007) The hypoxic tumour microenvironment, patient selection and hypoxia-modifying treatments. Clinical oncology (Royal College of Radiologists (Great Britain)) 19: 385-396). Both metabolic therapy and $HBO_2T$ have been used to inhibit cancer progression and enhance the efficacy of radiation and chemotherapy in animal models; however, additional evidence is needed to determine the potential use of these non-toxic adjuvant treatments (Stuhr, et al. (2004) Hyperbaric oxygen alone or combined with 5-FU attenuates growth of DMBA-induced rat mammary tumors. Cancer letters 210: 35-75; Bennett, et al. (2008) Hyperbaric oxygenation for tumour sensitisation to radiotherapy: a systematic review of randomised controlled trials. Cancer treatment reviews 34: 577-591; Stafford, et al. (2010) The ketogenic diet reverses gene expression patterns and reduces reactive oxygen species levels when used as an adjuvant therapy for glioma. Nutrition & metabolism 7: 74; Takiguchi, et al. (2001) Use of 5-FU plus hyperbaric oxygen for treating malignant tumors: evaluation of antitumor effect and measurement of 5-FU in individual organs. Cancer chemotherapy and pharmacology 47: 11-14; Moen, et al. (2009) Hyperoxia increases the uptake of 5-fluorouracil in mammary tumors independently of changes in interstitial fluid pressure and tumor stroma. BMC cancer 9: 446).

When ingested, KEs elevate blood ketone levels proportionally to the amount of ester taken (Clarke, et al. (2012) Kinetics, safety and tolerability of (R)-3-hydroxybutyl (R)-3-hydroxybutyrate in healthy adult subjects. Regulatory toxicology and pharmacology: RTP 63: 401-408; Desrochers, et al. (1995) Metabolism of (R,S)-1,3-butanediol acetoacetate esters, potential parenteral and enteral nutrients in conscious pigs. The American journal of physiology 268: E660-667; Clarke, et al. (2012) Oral 28-day and developmental toxicity studies of (R)-3-hydroxybutyl (R)-3-hydroxybutyrate. Regulatory toxicology and pharmacology: RTP 63: 196-208). 1,3-butanediol (BD), an approved, non-toxic food additive and hypoglycemic agent, is a compound metabolized by the liver to produce βHB and can also be used as a source of supplemental ketones (Kies, et al. (1973) Utilization of 1,3-butanediol and nonspecific nitrogen in human adults. The Journal of nutrition 103: 1155-1163; td. C (2003) 1,3-Butanediol IUCLID Data Set). We propose that supplemental ketone administration with KE or BD will inhibit cancer progression as a stand-alone treatment and also enhance the efficacy of ketogenic diet therapy. As described, in vitro, in vivo, and human studies all indicate that metabolic therapy targeting the abnormal energy metabolism of cancer cells is a promising direction in cancer research.

Energy metabolism is closely tied to the oxygen saturation state of the cell. Since oxygen is a vital component of ATP production via OXPHOS in the mitochondria, a decrease in tissue oxygen availability (hypoxia) induces a shift towards ATP production via SLP and glycolysis. The two primary cellular mechanisms that respond to hypoxic stress are the AMP-Activated Protein Kinase (AMPK) and Hypoxia-Inducible Factor-1 (HIF-1) pathways. AMPK works as an energy sensor by measuring the AMP:ATP ratio of the cell, a symbol of the cellular energy status. Hypoxia decreases mitochondrial ATP production, promoting activation of the AMPK pathway which stimulates catabolic processes such as fatty acid oxidation and glycolysis to provide energy substrates for the cell (Laderoute, et al. (2006) 5'-AMP-activated protein kinase (AMPK) is induced by low-oxygen and glucose deprivation conditions found in solid-tumor microenvironments. Molecular and cellular biology 26: 5336-5347). AMPK also induces the translocation of glucose transporters (GLUT-4) to the cell membrane, enhancing glucose uptake in tissues (Russell, et al. (1999) Translocation of myocardial GLUT-4 and increased glucose uptake through activation of AMPK by AICAR. The American journal of physiology 277: H643-649; Li J, et al. (2004) Role of the nitric oxide pathway in AMPK-mediated glucose uptake and GLUT4 translocation in heart muscle. American journal of physiology Endocrinology and metabolism 287: E834-841). HIF-1α is the primary oxygen sensing mechanism in the tissue. At normal tissue $PO_2$, HIF-1α is degraded, and the HIF-1 transcription factor remains sequestered and inactive in the cytoplasm. When tissues become hypoxic, HIF-1α is stabilized, activating HIF-1 which translocates to the nucleus, acting as a transcription factor for several hypoxia-responsive genes. Since this mechanism evolved to promote survival during transient hypoxic conditions, it is not surprising that many of the genes under regulation by HIF-1 are known oncogenes, promoting growth, cell survival, angiogenesis, and inhibiting apoptosis (Wouters, et al. (2004) Targeting hypoxia tolerance in cancer. Drug resistance updates: reviews and commentaries in antimicrobial and anticancer chemotherapy 7: 25-40; Le Q-T, Denko N, Giaccia A (2004) Hypoxic gene expression and metastasis. Cancer metastasis reviews 23: 293-310).

Tumors possess abnormal vasculature which blocks adequate tissue perfusion, leading to the presence of large hypoxic regions with abnormally low tissue oxygen saturation (Vaupel, et al. (2001) Treatment resistance of solid tumors: role of hypoxia and anemia. Medical oncology (Northwood, London, England) 18: 243-259). Healthy tissue oxygen tension varies by tissue type, but tumors contain hypoxic pockets expressing markedly lower $PO_2$ compared to their tissue of origin (Hoogsteen, et al. (2007) The hypoxic tumour microenvironment, patient selection and hypoxia-modifying treatments. Clinical oncology (Royal College of Radiologists (Great Britain)) 19: 385-396). While the average healthy tissue $PO_2$ is 55 mmHg, tumors possess an average tissue $PO_2$ of 8 mmHg, with 25% of tumors exhibiting less than 2.5 mmHg (Hoogsteen, et al. (2007) The hypoxic tumour microenvironment, patient selection and hypoxia-modifying treatments. Clinical oncology (Royal College of Radiologists (Great Britain)) 19: 385-396; Gill & Bell (2004) Hyperbaric oxygen: its uses, mechanisms of action and outcomes. QJM 97). This severe hypoxia confers many growth advantages to the cancer, mostly through the actions of HIF-1 which activates several oncogene pathways that promote cancer progression and metastasis, as seen in FIG. 2 (Vaupel & Harrison (2004) Tumor hypoxia: causative factors, compensatory mechanisms, and cellular response. The oncologist 9 Suppl 5: 4-9; Vaupel, et al. (2004) Tumor hypoxia and malignant progression. Methods in enzymology 381: 335-354). HIF-1 can also be activated by lactate; therefore, it is often functioning throughout the tumor due to the fermentative phenotype of cancer cells (Dhup, et al. (2012) Multiple biological activities of lactic acid in cancer: influences on tumor growth, angiogenesis and metastasis. Current pharmaceutical design 18: 1319-1330). Furthermore, tumor hypoxia has been shown to contribute to chemotherapy and radiation resistance (Vaupel & Harrison (2004) Tumor hypoxia: causative factors, compensatory mechanisms, and cellular response. The oncologist 9 Suppl 5: 4-9; Hoogsteen, et al. (2007) The hypoxic tumour microenvironment, patient selection and hypoxia-modifying treatments. Clinical oncology (Royal College of Radiologists (Great Britain)) 19: 385-396; Vaupel, et al. (2001) Treatment resistance of solid tumors: role of hypoxia and anemia. Medical oncology (Northwood, London, England) 18: 243-259; Vaupel, et al. (2004) Tumor hypoxia and malignant progression. Methods in enzymology 381: 335-354). Hypoxic cancer cells are three-times more resistant to radiation therapy than well-oxygenated cells (Gray, et al. (1953) The concentration of oxygen dissolved in tissues at the time of irradiation as a factor in radiotherapy. The British journal of radiology 26: 638-648).

As the present invention targets a metabolic phenotype that is present in most cancers regardless of the tissue of origin, i.e. the Warburg Effect, it is effective against any glycolytic cancer. The most common diagnostic tool that oncologists use is the FDG-PET scan, which scans for enhanced glucose uptake using the metabolic phenotype targeted by the invention, to diagnose nearly all types of cancers. Therefore, any cancer which utilizes this pathway, which is most, if not all cancers, is treatable using the present invention.

Combining metabolic therapy with $HBO_2T$ work synergistically to inhibit cancer progression. The addition of these non-toxic adjuvant therapies to the current standard of care has the potential to significantly improve the outcome of many patients with advanced metastatic disease.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
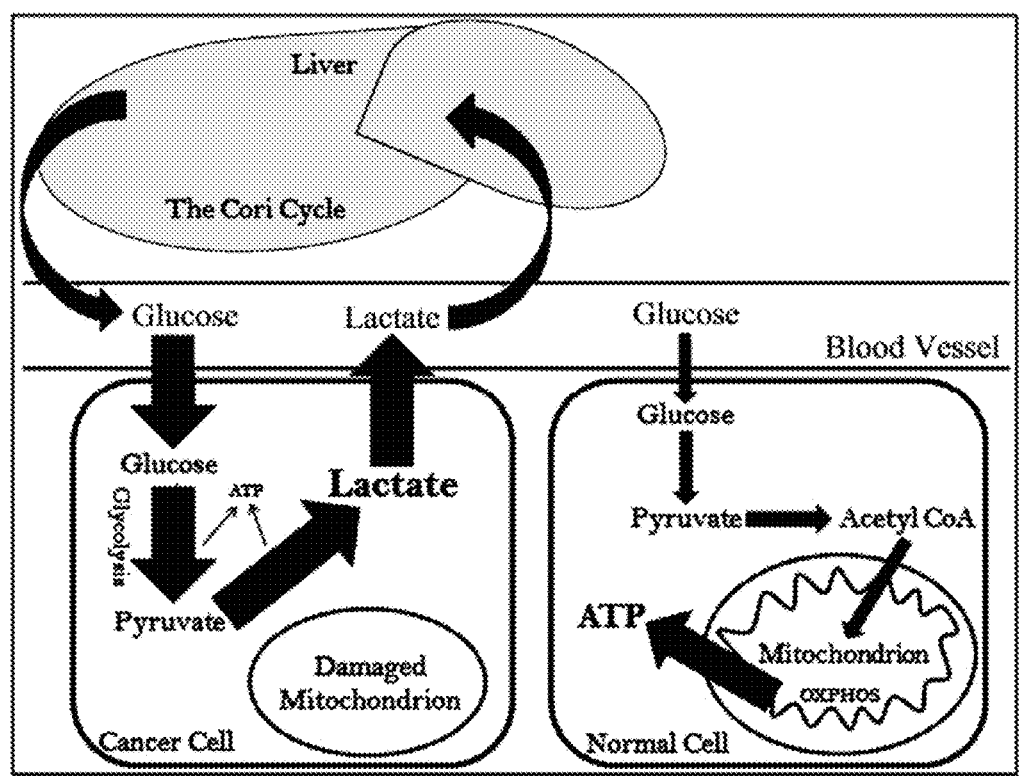
FIG. 1 is an illustration of energy metabolism of cancer cell compared to a normal cell.
Figure 2:
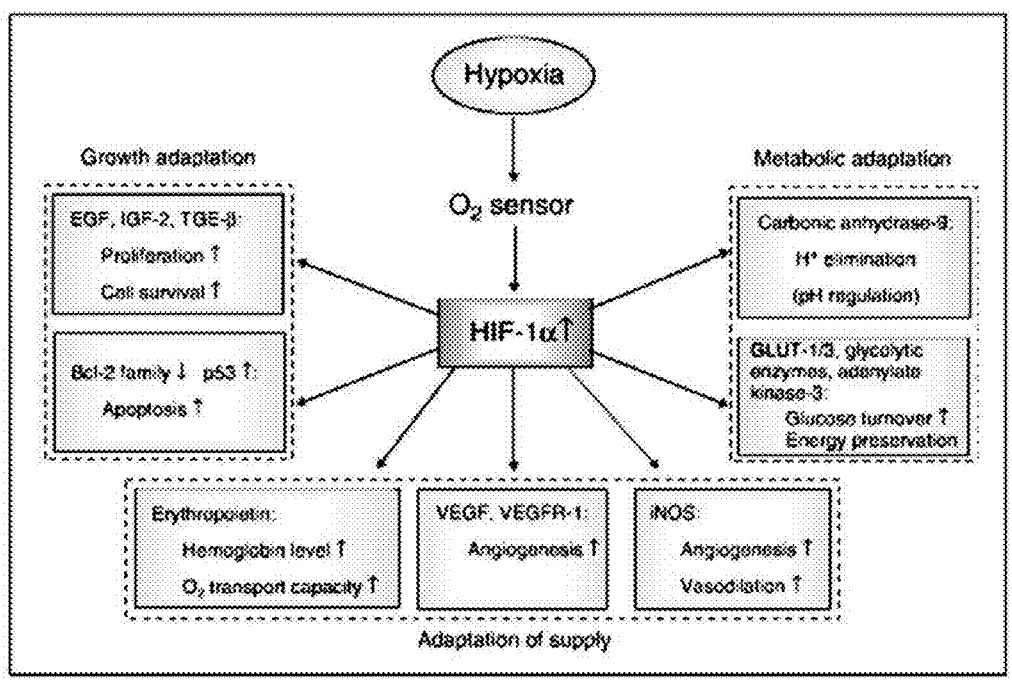
FIG. 2 is an illustration showing linking hypoxia to cancer progression. Image from Vaupel, P. et. al (Vaupel & Harrison (2004) Tumor hypoxia: causative factors, compensatory mechanisms, and cellular response. The oncologist 9 Suppl 5: 4-9).

ACA, acetoacetate; AFM, atomic force microscopy; AMPK, adenosine monophosphate kinase ATA, atmospheres absolute pressure (sea level=1 atmosphere, 33 feet of seawater, 760 mmHg); βHB, Beta-hydroxybutyrate; BD, 1,3-butanediol; $CO_2$, carbon dioxide; CR, calorie restriction; DER, dietary energy restriction; DHE, dihydroethidium; EH-1, Ethidium Homodimer-1; FI, fluorescence intensity; GBM, glioblastoma multiforme; HAFM, hyperbaric atomic force microscopy (AFM inside hyperbaric chamber); $H_2O_2$, hydrogen peroxide; $HBO_2$, hyperbaric oxygen; $HBO_2T$, hyperbaric oxygen therapy; HIF-1, hypoxia inducible factor-1; IGF-1, insulin-like growth factor 1; KD, ketogenic diet; KE, ketone ester; OXPHOS, oxidative phosphorylation; mTOR, mammalian target of rapamycin; MLP, membrane lipid peroxidation; PI3K, phosphoinositide-3 kinase; $PO_2$, oxygen partial pressure; PTEN, phosphatase and tensin homolog; ROS, reactive oxygen species; $.O_2^-$, superoxide anion; $R_a$, average roughness; t, time; SKA, supplemental ketone administration; SLP, substrate level phosphorylation; VEGF, vascular endothelial growth factor.

As used herein, the singular forms "a," "an" and "the" include plural referents unless the context clearly dictates otherwise. Thus, for example, reference to "a polypeptide" includes a mixture of two or more polypeptides and the like.

As used herein, "about" means approximately or nearly and in the context of a numerical value or range set forth means±15% of the numerical.

As used herein "animal" means a multicellular, eukaryotic organism classified in the kingdom Animalia or Metazoa. The term includes, but is not limited to, mammals. Non-limiting examples include rodents, aquatic mammals, domestic animals such as dogs and cats, farm animals such as sheep, pigs, cows and horses, and humans. Wherein the terms "animal" or "mammal" or their plurals are used, it is contemplated that it also applies to any animals.

As used herein, the term "cancer" or "cancerous" refer to or describe the physiological condition in mammals that is typically characterized by unregulated cell growth, i.e., proliferative disorders. Examples of such proliferative disorders include cancers such as carcinoma, lymphoma, blastoma, sarcoma, and leukemia, as well as other cancers disclosed herein. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, liver cancer, e.g., hepatic carcinoma, bladder cancer, colorectal cancer, endometrial carcinoma, kidney cancer, and thyroid cancer.

As used herein "glycolytic cancer" means a cancer cell which utilizes the glycolytic pathway as a sole means of energy production. The glycolytic pathway refers to overall process of the enzymatic breakdown of a carbohydrate with a resultant production of energy using the Embden-Meyerhof pathway sequence: glucose; glucose-6-phosphate; fructose-6-phosphate; fructose-1,6-diphosphate; dihydroxyacetone-phosphate; glyceraldehyde-3-phosphate; 1,3-diphosphoglycerate; 3-phosphoglycerate; 2-phosphoglycerate; phosphoenolpyruvate (PEP); pyruvate; acetaldehyde; and acetate. The TAC intermediates are succinate, oxalacetate, malate, fumarate, 2-keto-glutarate, isocitrate, and citrate.

As used herein the term "patient" is understood to include an animal, especially a mammal, and more especially a human that is receiving or intended to receive treatment.

As used herein, the term "effective amount" refers to the amount of a compound which is sufficient to reduce or ameliorate the progression and or severity of cancer or one or more symptoms thereof, prevent the development, recurrence or onset of pancreatic cancer or one or more symptoms thereof, prevent the advancement of pancreatic cancer or one or more symptoms thereof.

As used herein, the term "therapeutically effective amount" refers to that amount of a therapy (e.g., a chemotherapeutic agent) sufficient to result in the amelioration of pancreatic cancer or one or more symptoms thereof, prevent advancement of bladder cancer cause regression of bladder cancer, or to enhance or improve the therapeutic effect(s) of another therapy (e.g., chemotherapeutic agent).

Example 1

To determine the anti-cancer effects of KD metabolic therapy on cancer, survival time, rate of tumor growth, body weight, blood glucose, and blood ketones were measured in mice with VM-M3 metastatic cancer treated with KD, VM-M3/Fluc cells (T. Seyfried; Boston College) were obtained from a spontaneous tumor in a VM/Dk inbred mouse and adapted to cell culture (Huysentruyt et al., Metastatic cancer cells with macrophage properties: evidence from a new murine tumor model. Intl J Can. 2008, 123(1):73-84). The VM-M3 cells were identified from a spontaneous tumor in VM/dk inbred strain, and exhibit highly metastatic properties upon subcutaneous implantation, with rapidly metastasis throughout the model organism. VM-M3/Fluc cells are transfected with the firefly luciferase gene which produces a bioluminescent product in the presence of the enzymatic substrate luciferin (Shelton, et al. (2010) A novel pre-clinical in vivo mouse model for malignant brain tumor growth and invasion. Journal of neuro-oncology 99: 165-176). Bioluminescence can be detected and measured with the Xenogen IVIS Lumina System (Caliper LS). Intensity of bioluminescent signaling (photon count) is directly correlated to the number of luciferase-tagged cells within the animal (Kim, et al. (2010) Non-invasive detection of a small number of bioluminescent cancer cells in vivo. PloS one 5: e9364; Lim, et al. (2009) In vivo bioluminescent imaging of mammary tumors using IVIS spectrum. Journal of visualized experiments: JoVE) and is a well-accepted method of measuring tumor size in animals with luciferase-expressing tumors (Lyons (2005) Advances in imaging mouse tumour models in vivo. The Journal of pathology 205: 194-205; Close, et al. (2011) In vivo bioluminescent imaging (BLI): noninvasive visualization and interrogation of biological processes in living animals. Sensors (Basel, Switzerland) 11: 180-206). Mice received an i.p. injection of 50 mg/kg D-Luciferin 15 minutes prior to in vivo imaging. Bioluminescent signal was recorded using a 1 second exposure time on the IVIS Lumina cooled CCD camera. Progression of the metastatic cancer was measured by tracking the bioluminescent signal of the whole animal over time. Tumor bioluminescence will be measured once weekly for the duration of the study.

Adult male mice (2-4 months of age) were separated into treatment groups, as provided in Table 1. On day 0 of the study, 1 million VM-M3/Fluc cells in 300 µL PBS were subcutaneously implanted into the abdomen of male, 10-18 week old VM/Dk mice using a 27 g needle. With the VM-M3 model, an adipose tumor quickly appeared following inoculation and rapidly metastasized to most major organs, including brain, lungs, liver, spleen, kidneys, and bone marrow (Huysentruyt, et al. (2008) Metastatic cancer cells with macrophage properties: evidence from a new murine tumor model. International journal of cancer Journal international du cancer 123: 73-84). On the day of tumor inoculation, mice were randomly assigned to one of five study groups: Control, KD-Solace, KD-USF, KD-USF, standard diet with 1,3-Butanediol (SD+BD) standard diet with ketone ester (SD+KE), KD-Solace with 1,3-Butanediol (KD+BD), or KD-Solace with ketone ester (KD+KE).

TABLE 1 mouse feed groups for treatment

| Treatment group | Treatments (food and pressure treatment) |
|---|---|
| Control | Standard diet fed ad libitum; ambient pressure |
| KD-Solace | Commercially available (Ketovolve, Solace Nutrition) ketogenic food fed ad libitum; ambient pressure |
| KD-USF | Teklad Custom Research Ketogenic diet designed by researchers (Harlan Laboratories) fed ad libitum; ambient pressure |
| SD + BD | Standard diet fed ad libitum + 1,3-Butanediol |
| SD + KE | Standard diet fed ad libitum + ketone ester |
| KD + BD | KD-Solace fed ad libitum + 1,3-Butanediol |
| KD + KE | KD-Solace food fed ad libitum + ketone ester |

Control mice were fed standard rodent chow (2018 Teklad Global 18% Protein Rodent Diet, Harlan Laboratories) fed ad libitum. Mice on a diet therapy received their respective diet fed ad libitum in lieu of standard rodent chow. Mice in the KD-Solace treatment group received KD-Solace (Solace Nutrition) ketogenic diet food, mixed 1:1 with $H_2O$ to form a paste. Mice in the KD-USF treatment group received a Teklad Custom Research Diet (Harlan Laboratories) designed by the researchers. The macronutrient information of the diets used in this study is provided in Table 2. The macronutrient ratio of the custom designed KD-USF diet is similar to ketogenic diets with very low carbohydrate (VLC), containing a high percentage of MCT oil (30-40%) and high protein (22%). The KD-USF diet is notably more palatable to the mice. Diets will be continuously replaced to maintain freshness and allow mice to feed ad libitum.

TABLE 2

Macronutrient information for SD, KD-Solace, and KD-USFUSF.

| Macronutrient Information | Standard Diet (SD) | Ketovolve KD-Solace | Custom KD-USF |
|---|---|---|---|
| % Cal from Fat | 6.2 | 89.2 | 77.1 |
| % Cal from Protein | 18.6 | 8.7 | 22.4 |
| % Cal from Carbohydrate | 75.2 | 2.1 | 0.5 |
| Caloric Density | 3.1 Kcal/g | 7.12 Kcal/g | 4.7 Kcal/g |

Figure 3:
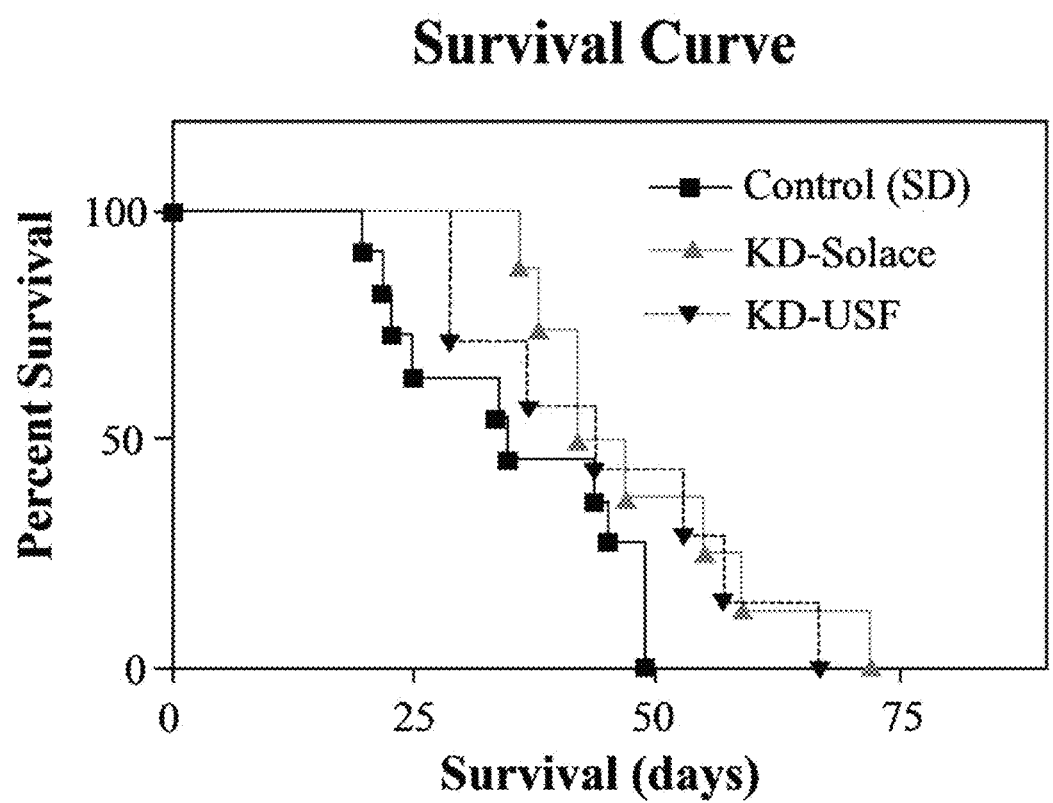
FIG. 3 is a Kaplan-Meier survival plot of study groups. KD-USF fed mice exhibited significantly longer mean survival times compared to control animals ($p<0.05$, Kaplan-Meier survival curve analysis).

Animal survival was analyzed with the Kaplan-Meier and Logrank Tests for survival distribution. Mean survival and cell viability were analyzed by two-tailed student's t-tests. KD administration increased mean survival, seen in FIG. 3 and Table 3, by approximately 15 days. Both ketone diets also increased mean survival time compared to control animals, as seen in Table 3 (Two-tailed student's t-test; *$p<0.05$). Control (SD) mice lived an average of 33.7 days while KD-Solace treated mice had a statistically significant mean survival time of 48.9 days, increasing survival time by 45.1% ($p>0.05$; Two-tailed student's t-test). KD-USF treatment increased mean survival time by approximately 12 days (33.8%) compared to controls, as seen in Table 3.

TABLE 3

The KD increases survival time and slows tumor growth in mice with systemic metastatic cancer. KD-USF fed mice exhibited significantly longer mean survival times compared to control animals ($p < 0.05$, student's t-test).

| Treatment | Cohort Size (N) | Mean Survival (days) | Increase in Survival Time |
|---|---|---|---|
| Control (SD) | 11 | 33.7 | — |
| KD-Solace | 8 | 48.9 | 45.1% |
| KD-USF | 7 | 45.1 | 33.8% |

Figure 4:
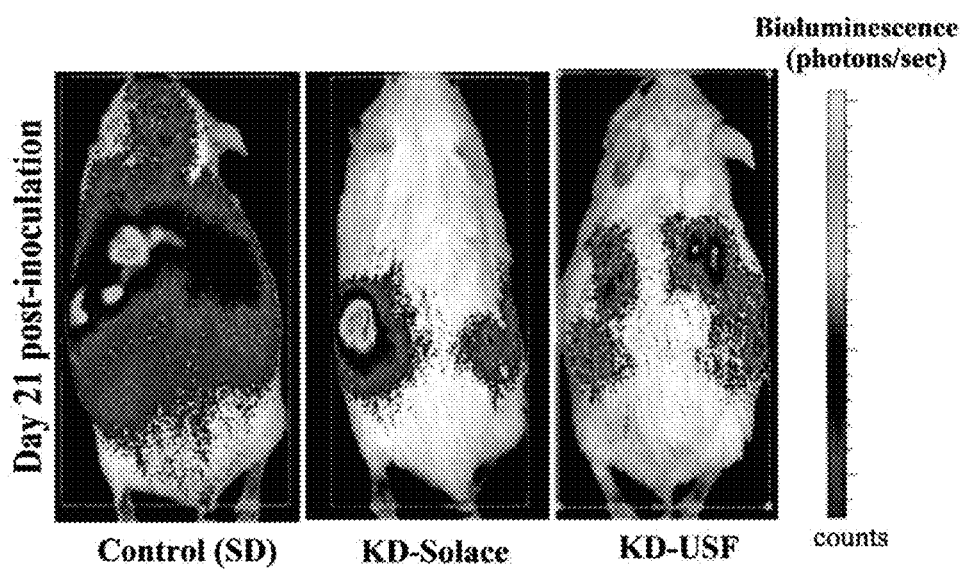
FIG. 4 are images showing metastatic spread represented by tumor bioluminescence. KD-fed mice exhibited noticeably less tumor bioluminescence than controls on day 21 post-inoculation.

Tumor progression was measured using bioluminescence on the Xenogen IVIS Lumina cooled CCD camera (Caliper LS, Hopkinton, Mass.). Bioluminescent signal of the luciferase-tagged cancer was acquired with the Living Image® software (Caliper LS). Mice received an i.p. injection of 50 mg/kg D-Luciferin (Caliper LS) 15 minutes prior to imaging. Bioluminescent signal was obtained using the IVIS Lumina cooled CCD camera system with a 1 sec exposure time. Whole animal bioluminescent signal was measured in photons/sec once a week as an indicator of metastatic tumor size and spread. Tumor progression was measured 21 days after tumor cell inoculation. As seen in FIG. 4, VM cells spread naturally in immunocompetent host mice. KD treatment, both KD-Solace and KD-USF, drastically reduced tumor progression, with KD-USF treatment also showing profound effect.

Figure 5:
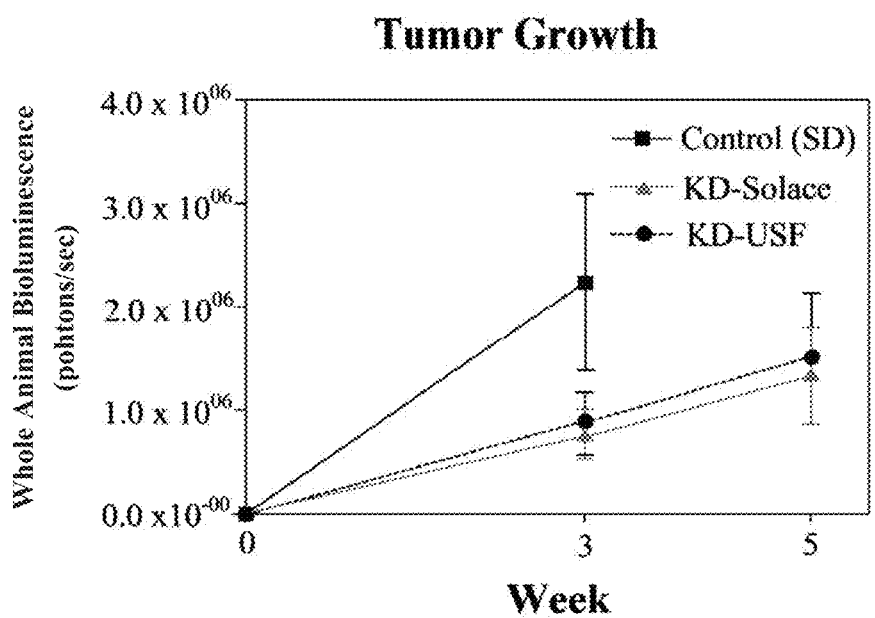
FIG. 5 is a graph showing bioluminescence shown as a function of time demonstrates the slower rate of tumor growth in KD-fed mice compared to controls.

Animals receiving the KD demonstrated a notable trend of slower tumor growth over time, with both KD-Solace and KD-USF treatments having similar growth rates as seen in FIG. 5. This trend reflected the increase in survival time seen in these animals.

Example 2

The anti-cancer effects of R,S-1,3-butanediol diacetoacetate ester (KE) and 1,3-butanediol (BD) as sources of supplemental ketones for metabolic therapy were determined for survival time, rate of tumor growth, body weight, blood glucose, and blood ketones.

Many cancers are unable to effectively utilize ketone bodies for energy (Maurer, et al. (2011) Differential utilization of ketone bodies by neurons and glioma cell lines: a rationale for ketogenic diet as experimental glioma therapy. BMC Cancer. 2011 Jul. 26; 11:315; Tisdale & Brennan (1983) Loss of acetoacetate coenzyme A transferase activity in tumours of peripheral tissues. British journal of cancer 47: 293-297; Magee, et al. (1979) The inhibition of malignant cell growth by ketone bodies. The Australian journal of experimental biology and medical science 57: 529-539). Furthermore, evidence suggests that ketones themselves possess inherent anti-cancer properties as βHB administration inhibits cancer cell proliferation and viability in vitro (Sawai, et al. (2004) Growth-inhibitory effects of the ketone body, monoacetoacetin, on human gastric cancer cells with succinyl-CoA: 3-oxoacid CoA-transferase (SCOT) deficiency. Anticancer research 24: 2213-2217; Magee, et al. (1979) The inhibition of malignant cell growth by ketone bodies. The Australian journal of experimental biology and medical science 57: 529-539). KDs are low carbohydrate, high fat diets that induce a modest elevation in blood ketone levels. R,S-1,3-butanediol-diacetoacetate ester (KE) is a non-ionized precursor to ketone bodies resulting in rapid elevation in ACA, and sustained elevation in βHB. 1,3-butanediol (BD) is a non-toxic food additive and hypoglycemic agent that is metabolized by liver to produce β-hydroxybutyrate. Both are potential food sources of supplemental ketone bodies which significantly elevate blood ketone concentrations regardless of diet (Desrochers, et al. (1995) Metabolism of (R,S)-1,3-butanediol acetoacetate esters, potential parenteral and enteral nutrients in conscious pigs. The American journal of physiology 268: E660-667; Kies, et al. (1973) Utilization of 1,3-butanediol and nonspecific nitrogen in human adults. The Journal of nutrition 103: 1155-1163; Puchowicz, et al. (2000) Dog model of therapeutic ketosis induced by oral administration of R,S-1,3-butanediol diacetoacetate. The Journal of nutritional biochemistry 11: 281-287; Brunengraber (1997) Potential of ketone body esters for parenteral and oral nutrition. Nutrition 13: 233-235; Tobin, et al. (1975) Nutritional and metabolic studies in humans with 1,3-butanediol. Federation proceedings 34: 2171-2176). To investigate the anti-cancer potential of ketones in vivo, the effects of supplemental ketone administration were tested alone and in combination with the KD on the VM-M3 mouse model of metastatic cancer.

Adult male mice (2-4 months of age) were separated into treatment groups, as provided in Table 4 and injected with 1 million VM-M3/Fluc cells into the abdomen of male, 10-18 week old VM/Dk mice as described in Example 1. On the day of tumor inoculation, mice were randomly assigned to one of the five study groups.

TABLE 4 mouse feed groups for treatment

| Treatment group | Treatments (food and pressure treatment) |
|---|---|
| SD (Control) | Standard diet fed ad libitum |
| SDKE | Standard diet + 20% KE fed ad libitum |
| SDBD | Standard diet + 20% BD fed ad libitum |
| KDKE | KD-USF ketogenic diet food + 10% KE fed ad libitum |
| KDBD | KD-Solace ketogenic diet food + 20% BD fed ad libitum |

Two sources of supplemental ketones were used in this study: the R,S-1,3-butanediol-diacetoacetate ester (Ketone Ester, KE) and 1,3-butanediol (BD). The KE was synthesized (Savind Inc., Seymour Ill.) as previously described (D'Agostino et al., Therapeutic ketosis with ketone ester delays central nervous system oxygen toxicity seizures in rats. Am J Physiol Regul Integr Comp Physiol 2013, 304 (10):R829-836) by transesterification of t-butylacetoacetate with R,S-1,3-butanediol (Savind Inc) and is a non-ionized, sodium-free, pH-neutral precursor of acetoacetate (ACA). The KE consists of two ACA molecules esterified to one molecule of 1,3-butanediol, an organic alcohol commonly used as a solvent in food flavoring agents. When ingested, gastric esterases rapidly cleave the KE to release two ACA molecules which are absorbed into circulation, rapidly elevating blood ketone concentration (Desrochers, et al. (1995) Metabolism of (R,S)-1,3-butanediol acetoacetate esters, potential parenteral and enteral nutrients in conscious pigs. The American journal of physiology 268: E660-667). The 1,3-butanediol molecule is absorbed and metabolized by the liver to produce βHB, providing a more sustained elevation of blood ketones. Administration of dietary BD is the second supplemental ketone source we will test, and it works to elevate ketone levels as previously described.

Control mice received standard rodent chow fed ad libitum. Mice receiving ketone supplementation diet therapy was administered their respective diet fed ad libitum in lieu of standard rodent chow. Saccharin was added to increase palatability and does not have a measurable effect on metabolism. Supplemental ketones may be unpalatable to the mice causing the mice to self-calorie restrict (Kashiwaya, et al. (2010) A ketone ester diet increases brain malonyl-CoA and Uncoupling proteins 4 and 5 while decreasing food intake in the normal Wistar Rat. The Journal of biological chemistry 285: 25950-25956). As previously described, DER is known to inhibit cancer progression in vivo. However, testing showed calorie restriction did not have a significant effect on cancer progression (data not shown).

SDKE mice received standard rodent chow mixed at 20% KE and 1% saccharin by volume. SDBD mice received standard rodent chow mixed at 20% BD and 0.1 to 1% saccharin by volume. KDKE mice received KD-USF ketogenic diet food mixed at 20% KE and 1% saccharin by volume. Mice in the KDBD treatment group received KD-Solace ketogenic diet food mixed at 20% BD, 29% $H_2O$ (to form a solid paste) and 0.1 to 1% saccharin by volume. See Table 5 for macronutrient information of diets and ketone supplements. Initial studies indicated that KD-Solace mixed with KE was severely unpalatable to the mice, so KD-USF mixed at 10% KE will be used for the KDKE group, since the KE was unpalatable to mice and was not consumed at 20% or when mixed with KD-Solace. Diets were continuously replaced to maintain freshness and allow mice to feed ad libitum.

TABLE 5

Macronutrient information for SD, KD-Solace, KD-USF, BD, and KE.

| Macronutrient Information | Standard Diet (SD) | Ketovolve KD-Solace | Custom KD-USF | 1,3-BD (BD) | Ketone Ester (KE) |
|---|---|---|---|---|---|
| % Cal from Fat | 6.2 | 89.2 | 77.1 | N/A | N/A |
| % Cal from Protein | 18.6 | 8.7 | 22.4 | N/A | N/A |
| % Cal from Carbohydrate | 75.2 | 2.1 | 0.5 | N/A | N/A |
| Caloric Density | 3.1 Kcal/g | 7.12 Kcal/g | 4.7 Kcal/g | 6.0 Kcal/g | 5.58 Kcal/g |

Blood was collected from the study animals every 7 days. Blood glucose and βHB concentrations were measured using a commercially available Glucose and Ketone (βHB) Monitoring System (Nova Biomedical and Abbott Laboratories). Mice were weighed twice weekly for the duration of the study using the AWS-1Kg Portable Digital Scale (AWS). Blood and weight measurements were taken at the same time of day each week to control for normal fluctuations in feeding or circadian metabolic changes. Studies will focus on health and behavior of the animals on a daily basis. Survival time was measured as the time in days from cancer cell inoculation to presentation of defined criteria (diminished response to stimuli, loss of grooming or feeding behavior, lethargy, severe ascites, or failure to thrive). At that time, mice were humanely euthanized by $CO_2$ asphyxiation and survival time noted.

Supplemental ketone administration was expected to increase survival time, slow tumor growth rate, decrease blood glucose, and elevate blood ketones in VM-M3 mice with metastatic cancer compared to control animals. Since the KE supplies more ketones to the tissues than BD, and ketones inhibit cancer cell proliferation in vitro (Sawai, et al. (2004) Growth-inhibitory effects of the ketone body, monoacetoacetin, on human gastric cancer cells with succinyl-CoA: 3-oxoacid CoA-transferase (SCOT) deficiency. Anti-cancer research 24: 2213-2217; Magee, et al. (1979) The inhibition of malignant cell growth by ketone bodies. The Australian journal of experimental biology and medical science 57: 529-539), it was expected that the anti-cancer effects of the supplemental ketone administration would be greater in KE-fed mice. Further, since carbohydrate restriction decreases blood glucose which cancer cells rely on for energy, combining KE or BD with a ketogenic diet was expected to be more effective than when combined with standard diet.

Figure 6:
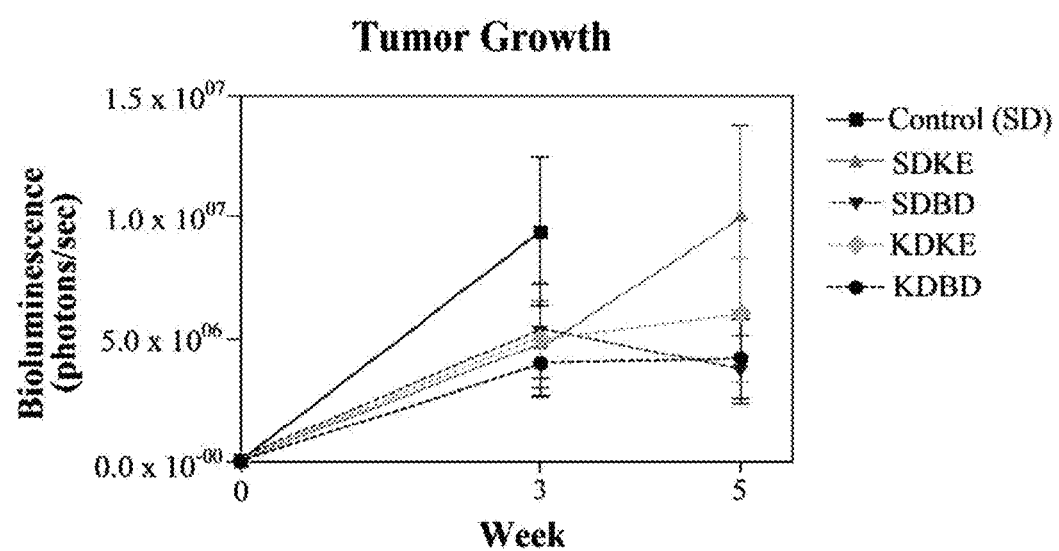
FIG. 6 is a graph showing animals in the treatment groups showed slower tumor growth than controls. Total body bioluminescence was measured weekly as a measure of tumor size; error bars represent ±SEM.
Figure 7:
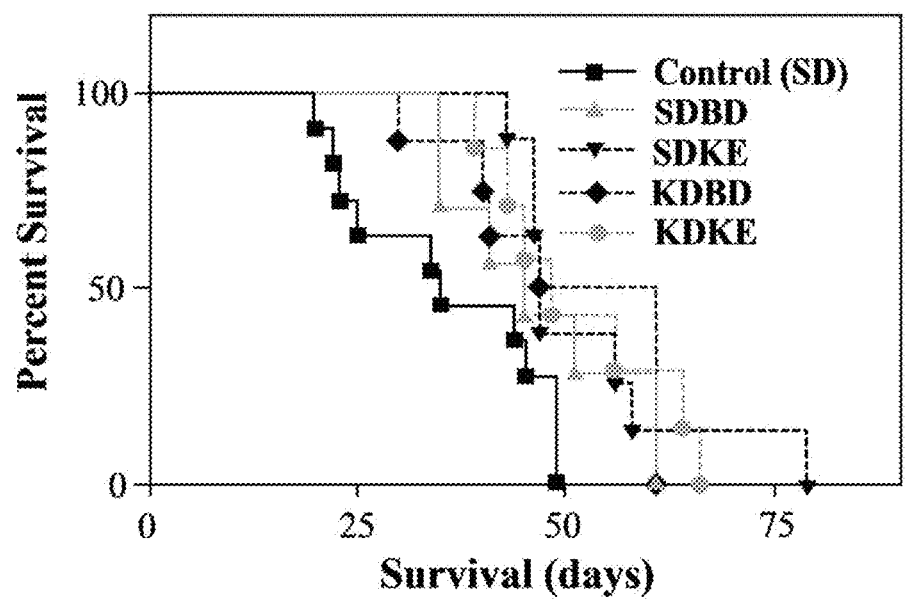
FIG. 7 is a Kaplan-Meier survival plot graph of study groups showing supplemental ketone administration increases survival time in mice with systemic metastatic cancer. All treatment groups exhibited a significantly different survival from control animals by the Logrank Survival Test ($p=0.05$) and significant increases in mean survival time means compared to control animals by two-tailed student's t-test ($p<0.05$).
Figure 8:
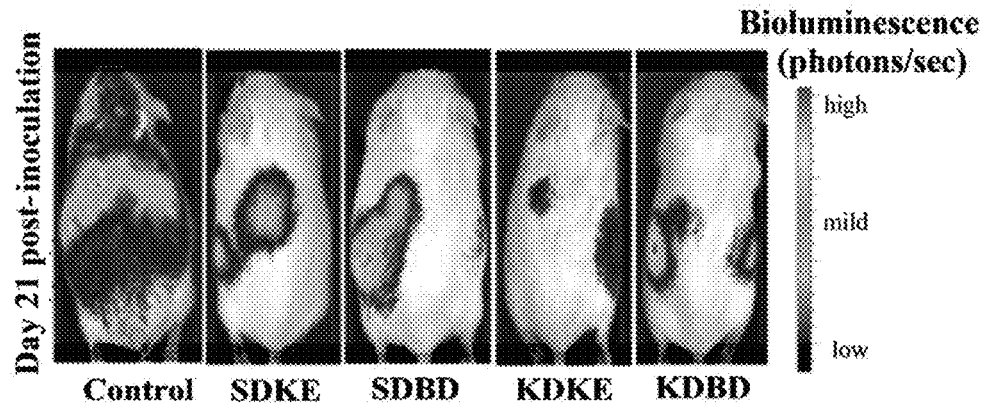
FIG. 8 are images showing ketone supplementation increases survival time and slows tumor growth in mice with systemic metastatic cancer. Metastatic spread represented by tumor bioluminescence. Ketone supplement-fed mice exhibited noticeably less tumor bioluminescence than controls on day 21 post-inoculation.

Animals receiving supplemental KD exhibited reduced tumor growth, seen in FIG. 6, and increased mean survival, seen in FIG. 7 and Table 6. Bioluminescent signal of the luciferase-tagged cancer was measured 21 days after tumor cell inoculation. As seen in FIG. 8, VM cells metastasized throughout the control animals. Supplementation with KE or BD greatly reduced tumor growth and reduced metastasis of the tumor, as shown by luciferase signal focused in the abdomen. Further, KD treatment, with KE supplementation, drastically reduced tumor progression with profound effect. While BD supplementation to KD did reduce rumor progression, even more than BD supplementation alone, the effects were considerably less than those seen with KE supplementation, as seen in FIG. 8.

TABLE 6

The supplemental ketogenic diet increased survival time in mice with systemic metastatic cancer. The treatment cohort group and median survival times are shown.

| Treatment | Cohort size (N) | Mean survival (days) | % increase in survival time |
|---|---|---|---|
| control (SD) | 10 | 35.1 | — |
| SDKE | 8 | 52.8 | 50.4* |
| SDBD | 7 | 47 | 33.9* |
| KDKE | 7 | 51.6 | 47.0* |
| KDBD | 8 | 50.3 | 43.3* |

*p < 0.05

Figure 9:
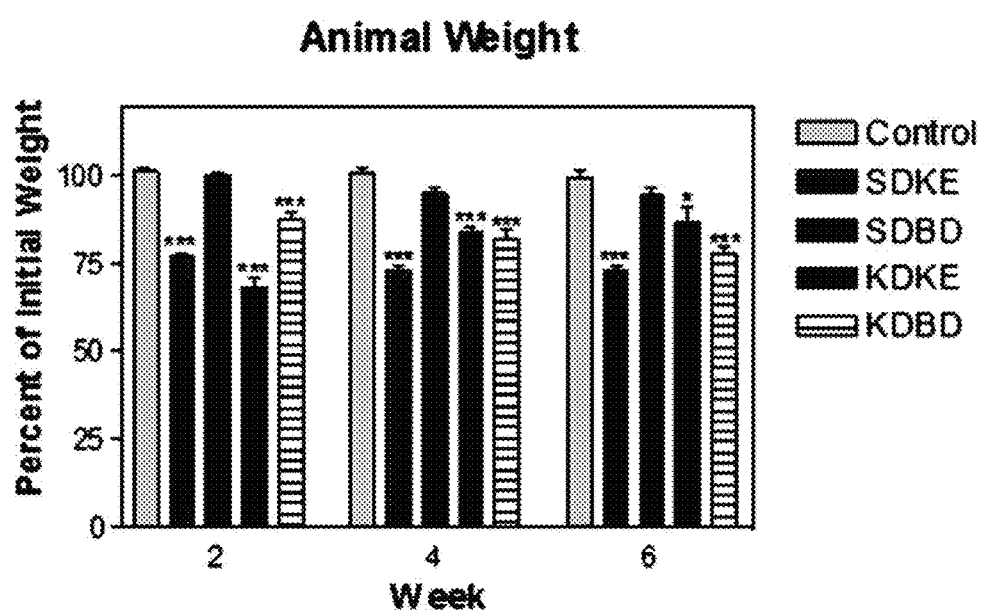
FIG. 9 is a graph showing animal weight. The graph bars indicate average percent of initial body weight for animals at weeks 2, 4, and 6. Error bars represent ±SEM.
Figure 10:
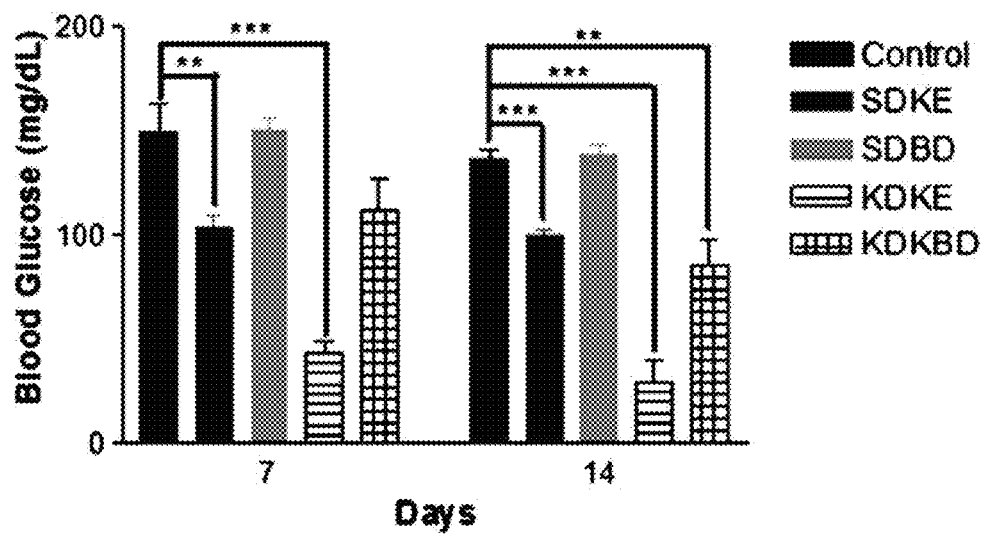
FIG. 10 is a graph showing blood glucose levels in animals. Mice receiving supplemental ketone ester (SDKE and KDKE) showed significantly lower glucose than controls on day 7 ($p<0.01$). Animals in the SDKE, KDKE, and KDBD groups had significantly lower blood glucose levels than controls on day 14 ($p<0.01$).
Figure 11:
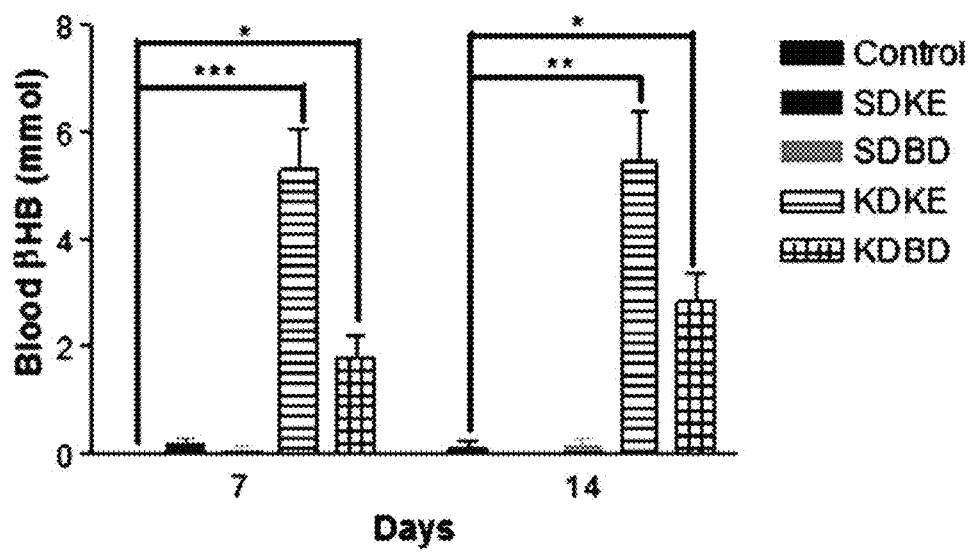
FIG. 11 is a graph showing β-hydroxybutyrate levels in animals. KDKE and KDBD groups had significantly higher blood ketones than controls on both day 7 and day 14 ($p<0.05$).

Supplementation of food with 20% KE (SDKE) or KD-USF ketogenic diet food mixed with 20% KE (KDKE) significantly reduced mouse weight at week 2, with KDKE mice normalizing slightly in weeks 4 and 6, as seen in FIG. 9. KD-Solace ketogenic diet food with 20% BD (KDBD) also exhibited decreased animal weight compared to control and rodent chow mixed with 20% BD (SDBD), though less dramatic than SDKE, as seen in FIG. 9. Blood glucose levels mirrored animal weight correlations, with SDKE, KDKE, and KDBD showing reduced glucose levels compared to controls, as seen in FIG. 10. Unlike the KD treatments disclosed in Example 1, ketone supplementation resulted in significantly higher ketone levels in KDKE and KDBD, at both 7 and 14 days, as seen in FIG. 11.

It was concluded that supplemental ketone administration confers anti-cancer effects when delivered with either standard or ketogenic diet. SDBD mice did not show significant loss of weight but still had effects, indicating that ketones did induce significant results.

Example 3

To determine the anti-cancer effects of KD metabolic therapy and $HBO_2T$, survival time, rate of tumor growth, body weight, blood glucose, and blood ketones were measured in mice with VM-M3 metastatic cancer treated with KD, $HBO_2T$, or combined KD+$HBO_2T$.

As shown above, KD is useful as a metabolic therapy for cancer by reducing availability of glucose, the main energy substrate for tumors, and inhibiting several oncogene pathways such as IGF-1, MYC, mTOR, and Ras. $HBO_2T$ increases oxygen saturation inside tissues, reversing the cancer-promoting effects of tumor-hypoxia and enhancing ROS production which can induce cell death (D'Agostino, et al. (2009) Acute hyperoxia increases lipid peroxidation and induces plasma membrane blebbing in human U87 glioblastoma cells. Neuroscience 159: 1011-1033). While these therapies have been evaluated separately, the overlapping mechanisms mediating their efficacy are significantly enhanced by combining the treatments. Furthermore, even though metastasis is responsible for 90% of cancer deaths, few studies have evaluated metabolic therapy or $HBO_2T$ as a treatment for metastatic cancer. Therefore, the individual and combined anti-cancer effects of the ketogenic diet and $HBO_2T$ were evaluated in the VM-M3 mouse model of metastatic cancer (Huysentruyt, et al. (2008) Metastatic cancer cells with macrophage properties: evidence from a new murine tumor model. International journal of cancer Journal international du cancer 123: 73-84).

Adult male mice (2-4 months of age) were injected subcutaneously in the abdomen with 1 million VM-M3/Fluc cells, as described in Example 1. On the day of tumor inoculation, mice were randomly assigned to a treatment group, as provided in Table 7. With the VM-M3 model, an adipose tumor quickly appeared following inoculation and rapidly metastasized to most major organs, including brain, lungs, liver, spleen, kidneys, and bone marrow (Huysentruyt, et al. (2008) Metastatic cancer cells with macrophage properties: evidence from a new murine tumor model. International journal of cancer Journal international du cancer 123: 73-84).

TABLE 7 mouse feed groups for treatment

| Treatment group | Treatments (food and pressure treatment) |
|---|---|
| Control | Standard diet fed ad libitum; ambient pressure |
| KD-Solace | Commercially available (Ketovolve, Solace Nutrition) ketogenic food fed ad libitum; ambient pressure |
| KD-USF | Teklad Custom Research Ketogenic diet designed by researchers (Harlan Laboratories) fed ad libitum; ambient pressure |
| SD + $HBO_2T$ | Standard diet fed ad libitum + $HBO_2T$ |
| KD + $HBO_2T$ | KD-Solace food fed ad libitum + $HBO_2T$ |

Control mice were fed standard rodent chow (2018 Teklad Global 18% Protein Rodent Diet, Harlan Laboratories) fed ad libitum. Mice on a diet therapy received their respective diet fed ad libitum in lieu of standard rodent chow. Mice in the KD-Solace treatment group received KD-Solace (Solace Nutrition) ketogenic diet food, mixed 1:1 with $H_2O$ to form a paste. Mice in the KD-USF treatment group received a Teklad Custom Research Diet (Harlan Laboratories) designed by the researchers. The macronutrient information of the diets used in this study is provided in Table 8. The macronutrient ratio of the custom designed KD-USF diet is similar to ketogenic diets with very low carbohydrate (VLC), containing a high percentage of MCT oil (30-40%) and high protein (22%). The KD-USF diet is notably more palatable to the mice. Diets will be continuously replaced to maintain freshness and allow mice to feed ad libitum.

TABLE 8

Macronutrient information for SD, KD-Solace, and KD-USF.

| Macronutrient Information | Standard Diet (SD) | Ketovolve KD-Solace | Custom KD-USF |
|---|---|---|---|
| % Cal from Fat | 6.2 | 89.2 | 77.1 |
| % Cal from Protein | 18.6 | 8.7 | 22.4 |
| % Cal from Carbohydrate | 75.2 | 2.1 | 0.5 |
| Caloric Density | 3.1 Kcal/g | 7.12 Kcal/g | 4.7 Kcal/g |

Mice in the SD+$HBO_2T$ and KD+$HBO_2T$ treatment groups received $HBO_2T$ (100% oxygen) at 2.5 ATA absolute (1.5 ATA gauge) for 90 minutes three times a week (M, W, F) pressurized in a hyperbaric chamber.

Figure 12:
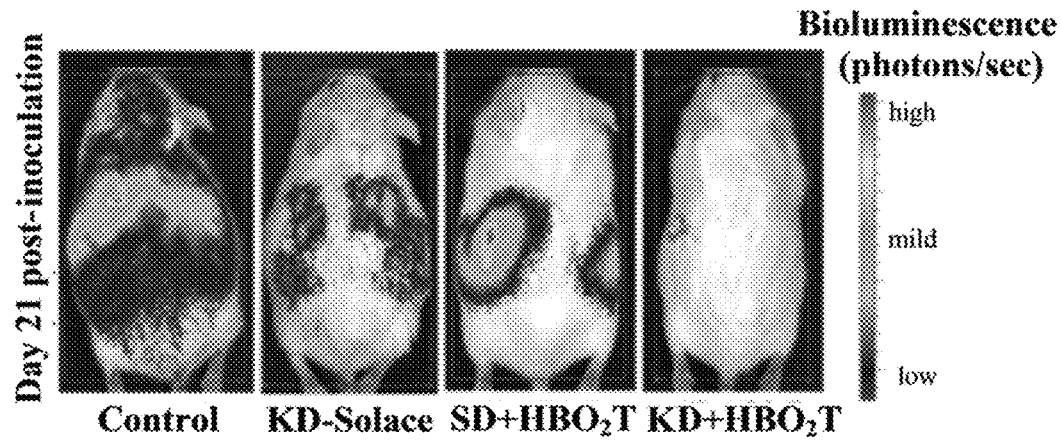
FIG. 12 are images showing ketogenic diet and hyperbaric oxygen therapy work synergistically to slow cancer progression. Metastatic spread and tumor growth rate was dramatically decreased.
Figure 13:
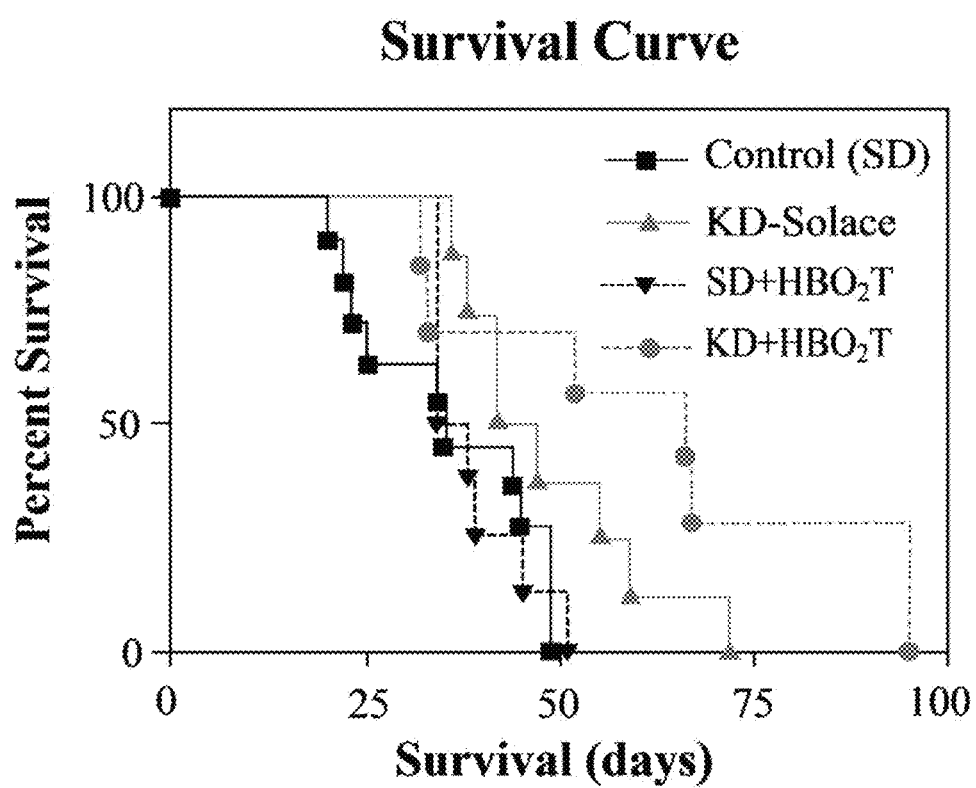
FIG. 13 is a graph showing ketogenic diet and hyperbaric oxygen therapy work synergistically to slow cancer progression. Mice receiving combined therapy demonstrated significantly longer survival curves and increased mean survival time compared to controls ($p<0.05$, Kaplan-Meier survival curve analysis). The effect was supra-additive compared to either therapy alone, indicating a synergistic mechanism of action.
Figure 14:
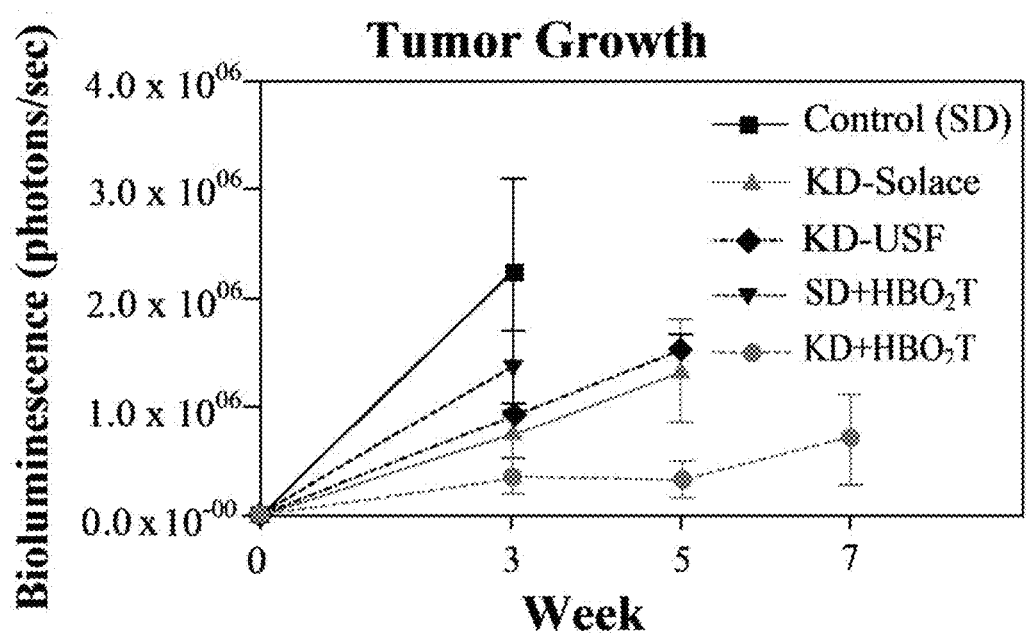
FIG. 14 is a graph showing animals in the treatment groups showed slower tumor growth than controls. Total body bioluminescence was measured weekly as a measure of tumor size; error bars represent ±SEM.

Bioluminescent signal of the luciferase-tagged cancer was measured 21 days after tumor cell inoculation. As in the previous Examples, VM cells metastasized throughout the control animals, with KD treatment greatly reducing tumor growth reduced metastasis, seen in FIG. 12. Hyperbaric treatment had a minor effect on reducing tumor growth, whereas the combined treatment using KD and hyperbaric therapy significantly and drastically reduced tumor progression with profound effect, with tumor cells localized to the injection site. Mirroring the bioluminescence studies, animals treated with KD had increased survival time compared to control and hyperbaric-only treated mice, by approximately 14 days, and combined KD-hyperbaric treatment increased survival by approximately 40 days compared to the control and hyperbaric-only treatment, as seen in FIG. 13. Due to the metabolic therapy and $HBO_2T$ target overlapping pathways, combining the KD with $HBO_2T$ were found to result in a synergistic decrease in tumor growth rate and increase in survival, as seen in FIG. 14 and Table 9. The effect was supra-additive compared to either therapy alone, indicating a synergistic mechanism of action.

TABLE 9

Treatment group cohort size and median survival times. KD-Solace mice exhibited a 34% increase in mean survival time compared to controls (p = 0.0249); KD-$HBO_2T$ mice exhibited an 80% increase in mean survival time compared to controls (p = 0.0082).

| Treatment | Cohort size (N) | Mean survival (days) | % increase in survival time |
| --- | --- | --- | --- |
| control (SD) | 10 | 35.1 | — |
| KD-Solace | 8 | 48.9 | 39.3* |
| KD-USF | 7 | 45.1 | 28.5 |
| SD + $HBO_2T$ | 8 | 38.8 | 10.5 |
| KD + $HBO_2T$ | 7 | 62.9 | 80** |

*p < 0.05
**p < 0.001

Blood was collected from the study animals every 7 days. Blood glucose and βHB concentrations were measured using a commercially available glucose and ketone (βHB) Monitoring System (Nova Biomedical and Abbott Laboratories). Mice were weighed twice weekly for the duration of the study using the AWS-1 Kg Portable Digital Scale (AWS). Blood and weight measurements were taken at the same time of day each week to control for normal fluctuations in feeding or circadian metabolic changes. Survival time was measured as the time in days from cancer cell inoculation to presentation of defined criteria (diminished response to stimuli, loss of grooming or feeding behavior, lethargy, severe ascites, or failure to thrive). At that time, mice were humanely euthanized by $CO_2$ asphyxiation and survival time noted.

Figure 15:
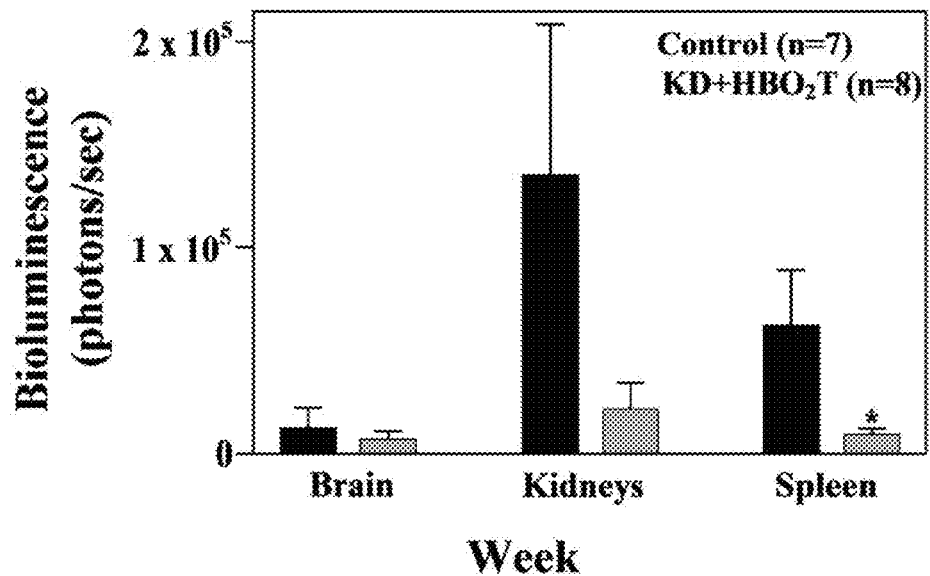
FIGS. 15(A) and (B) are graphs showing ketogenic diet and hyperbaric oxygen therapy work synergistically to slow cancer progression. Mice receiving combined therapy demonstrated dramatically decreased metastatic spread and tumor growth rate. The effect was supra-additive compared to either therapy alone, indicating a synergistic mechanism of action.
Figure 15:
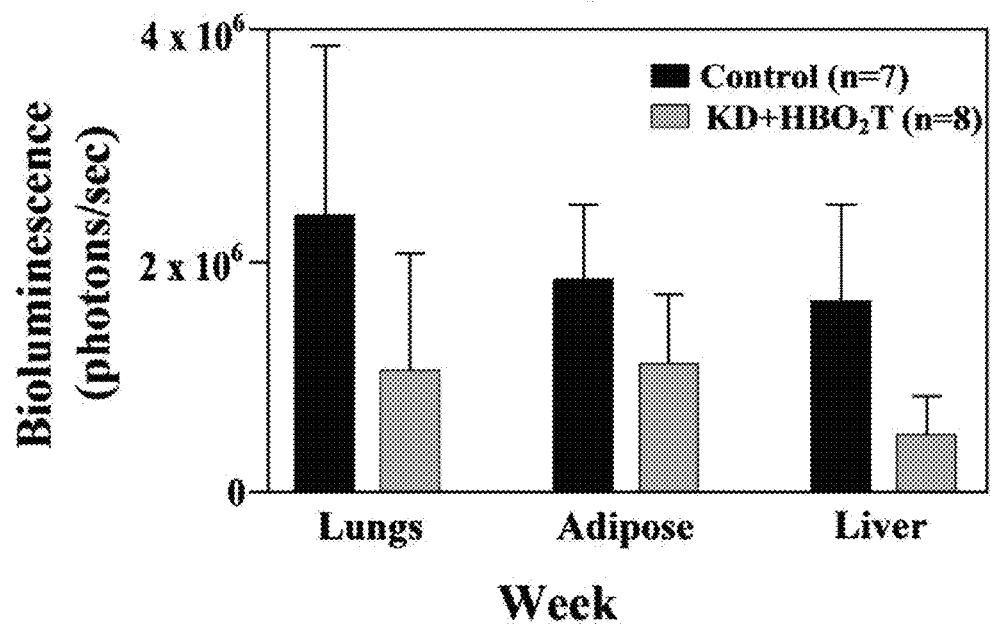

Tumor metastasis was analyzed in greater detail by harvesting the brain, kidneys, lungs, spleen, liver and adipose tissue after euthanization. As seen in FIGS. 15(A) and (B), combined KD-hyperbaric treatment reduced metastasis compared to control, with the kidneys, spleen, and liver showing drastically reduced tumor cell invasion, and reduced tumor cell invasion in the lungs and liver. Due to the blood brain barrier, tumor metastasis was very limited into the brain in both controls and KD-hyperbaric treated animals.

Figure 16:
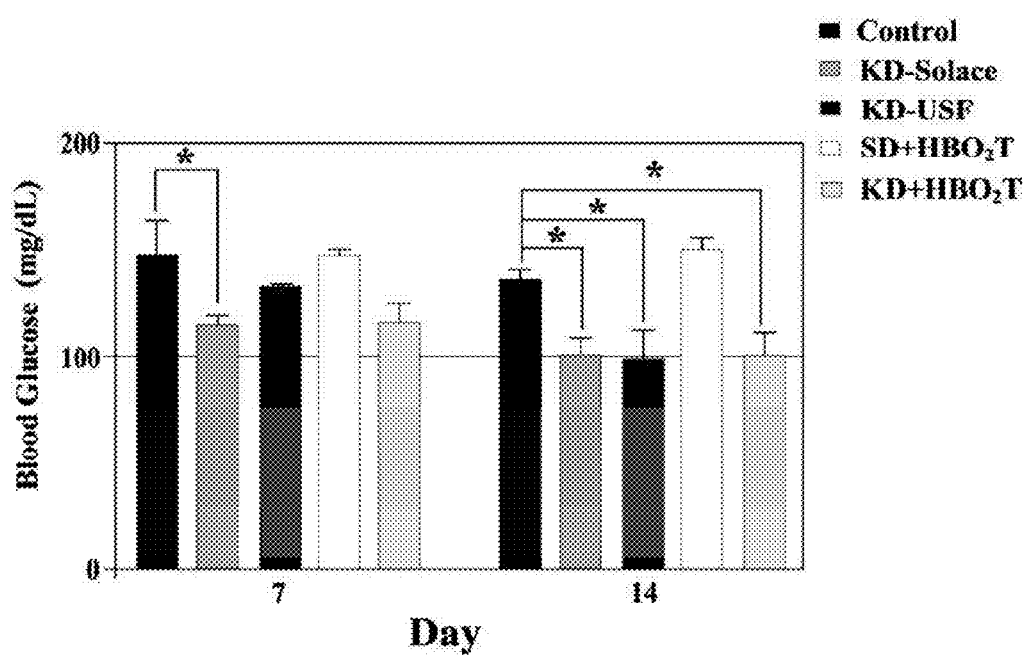
FIG. 16 is a graph showing blood and glucose levels in animals. KD mice showed significantly lower glucose than controls on day 7 ($p<0.05$). Animals in the KD-Solace, KD-USF, and $KD+HBO_2T$ groups had significantly lower blood glucose levels than controls on day 14 ($p<0.05$).
Figure 17:
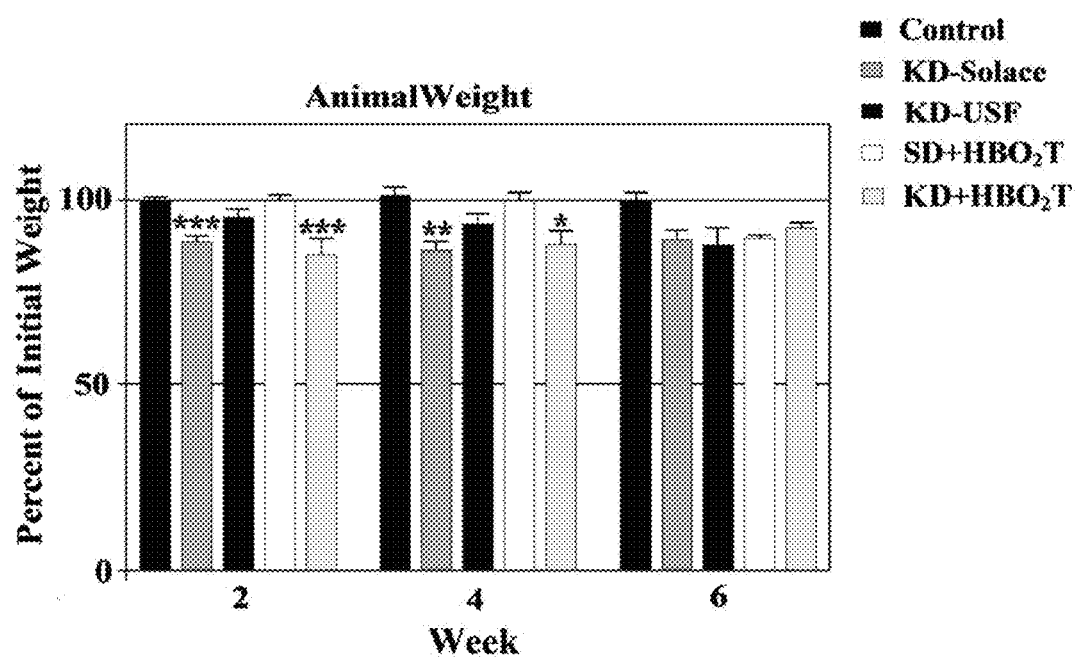
FIG. 17 is a graph showing animal weight. The graph bars indicate average percent of initial body weight for animals at weeks 2, 4, and 6. Error bars represent ±SEM.
Figure 18:
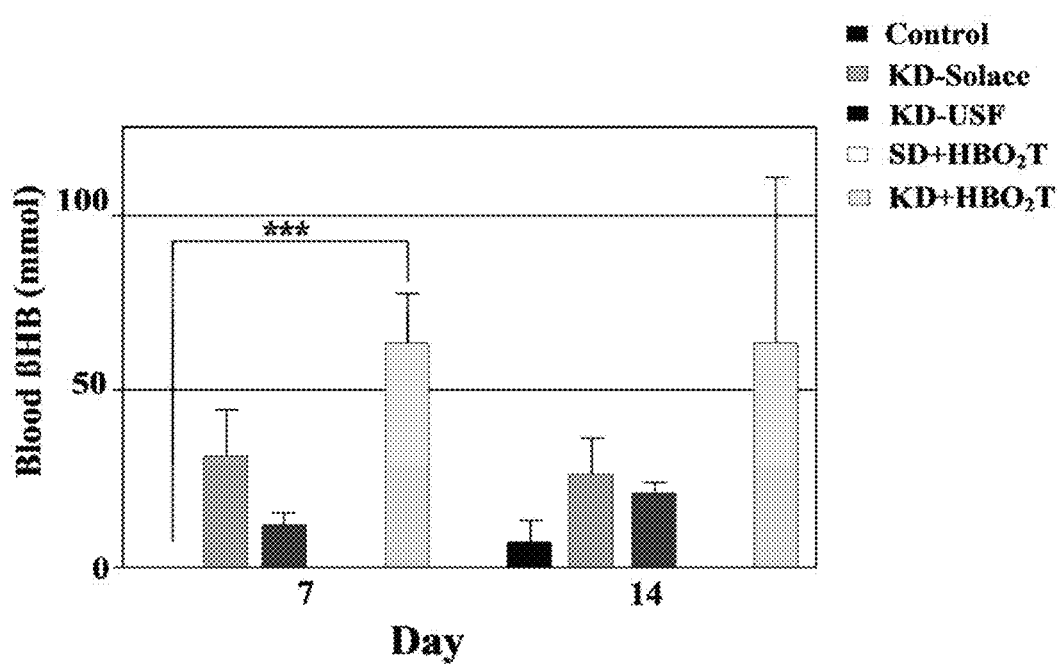
FIG. 18 is a graph showing β-hydroxybutyrate levels in animals. $KD+HBO_2T$ mice had significantly higher blood ketones than controls on day 7 ($p<0.001$). KD-Solace, KD-USF, and $KD+HBO_2T$ mice exhibited a trend of elevated ketones on day 14, but were not significantly different from controls.

Animals receiving KD had lower glucose, and some body weight loss compared to controls, as seen in FIGS. 16 and 17, respectively. While it was expected that KD treatment would result in higher ketones, results showed a transitory increase in blood ketones, with a non-significant difference at 14 days, as seen in FIG. 18.

Most studies examining the effects of $HBO_2T$ on cancer have focused on solid, primary tumors. Since hypoxia is most prevalent inside large tumors, it is possible that $HBO_2T$ would not be as effective a treatment for metastatic disease compared to solid tumors. When given as individual therapies, the KD but not $HBO_2T$ elicited anti-cancer effects in mice with systemic metastatic cancer. However, combining the KD with $HBO_2T$ elicited profound, supra-additive anti-cancer effects, indicating a synergistic mechanism of action.

Example 4

Determine the Synergistic Potential of Combining Supplemental Ketones with $HBO_2T$ as a Treatment for Metastatic Cancer To determine if supplemental ketone metabolic therapy and $HBO_2T$ work synergistically to inhibit the progression of metastatic cancer, survival time, rate of tumor growth, body weight, blood glucose, and blood ketones were measured in mice receiving supplemental ketones with $HBO_2T$. To further assess this combination therapy, the extent of organ metastasis in time-matched tumors, blood vessel density, and protein expression of important cancer signaling molecules were examined in VM-M3 mouse tumors ex vivo following treatment with the proposed therapies.

Data indicate that individually, the KD and ketone supplementation inhibit cancer progression, and that combining the KD with $HBO_2T$ had profound synergistic anti-cancer effects. KDKE mice exhibited the lowest blood glucose and highest blood ketone levels of the treatment groups. As previously discussed, lowering blood glucose and elevating blood ketones work through several mechanisms to inhibit cancer growth. Furthermore, KDKE therapy resulted in greater anti-cancer effects than the KD alone. Since KD combined with $HBO_2T$ induced supra-additive anti-cancer effects and KDKE therapy was more efficacious than KD-alone, combining the KDKE diet therapy with $HBO_2T$ elicited an even greater response. To determine the efficacy of these combined treatments, the survival, rate of tumor growth, body weights, blood glucose, and blood ketones was studied in VM-M3 mice receiving KDKE+$HBO_2T$ therapy. To further investigate the synergistic effects of KD, supplemental ketones, and $HBO_2T$ treatment on metastatic cancer, the extent of organ metastasis, blood vessel density, and protein expression of important signaling molecules in tumors ex vivo was measured from VM-M3 mice receiving KD+$HBO_2T$, KDKE, and KDKE+$HBO_2T$ therapies compared to control animals.

The mechanism of the anti-cancer effects of metabolic therapy and $HBO_2T$ were analyzed using VM-M3 mouse tumors ex vivo. On day 0 of the study, 1 million VM-M3/Fluc cells in 300 μL PBS are subcutaneously implanted into the abdomen of male, as described in the previous example, and randomly assigned to one of the four study groups; SD (Control)—Standard rodent chow fed ad libitum; KD+$HBO_2T$—KD-Solace ketogenic diet fed ad libitum+$HBO_2T$; KDKE—KD-USF ketogenic diet with 10% ketone ester fed ad libitum; or KDKE+$HBO_2T$—KD-USF ketogenic diet with 10% ketone ester fed ad libitum+$HBO_2T$. Mice in the control group receive standard rodent chow fed ad libitum. Mice in the KD+$HBO_2T$ group receive KD-Solace ketogenic food fed ad libitum. Mice in the KDKE and KDKE+$HBO_2T$ groups receive KD-USF ketogenic diet food mixed at 10% KE and 1% saccharin by volume fed ad libitum.

On day 21 of the study, mice are euthanized by $CO_2$ asphyxiation and brain, heart, lungs, liver, kidneys, spleen, intestine, and samples of adipose tissue and skeletal muscle will be surgically removed. Immediately following tissue extraction, organs are incubated in 300 μg/mL D-Luciferin in PBS for 5 min. Bioluminescence of the individual organs is imaged using a 1 second exposure time on the Xenogen IVIS Lumina cooled CCD camera (Caliper LS). Metastatic spread is analyzed by measuring intensity of bioluminescent signal (photon count) produced by the organs. Tissues are immediately flash frozen in liquid nitrogen to preserve viability for vessel density and protein expression studies.

Flash frozen hepatic tumor tissue are embedded in OCT compound and cut with a cryostat to produce 10 μm tissue sections for analysis of blood vessel density. Sections are mounted onto histological slides and stained with anti-mouse von Willibrand factor (vWf), an endothelial cell-specific glycoprotein, staining blood vessels brown. Slides are visualized and blood vessel density will be determined by counting the number of vWf+ blood vessels within a region of interest in a blinded manner.

Lung tumor protein expression of Insulin-like Growth Factor-1 (IGF-1), Activated Akt, Activated Mammalian Target of Rapamycin (mTOR), Hypoxia-Inducible Factor-1α (HIF-1α), and Vascular Endothelial Growth Factor (VEGF) are measured by standard western blot techniques using Anti-IGF-1, Anti-Phospho-Akt, Anti-Phospho-mTOR, Anti-HIF-1α, and Anti-VEGF antibodies (Sigma-Aldrich). Protein density will be determined using the GE Typhoon 9400 Imager with ImageQuant TL software (GE Life Sciences).

Combining the KD with $HBO_2T$ or KE confers potent anti-cancer effects in our model; therefore, KDKE+$HBO_2T$ treated mice should demonstrate even greater efficacy with increased survival time and decreased tumor growth rate. All treated mice should demonstrate reduced organ metastasis compared to control animals although it is unclear if this will be due to inhibition of primary tumor growth or effects on the metastatic process itself. Animals treated with $HBO_2T$ will likely demonstrate significantly less tumor vasculature, as hyperoxia inhibits many angiogenic factors known to be overactive in cancer. The proposed signaling molecules should be elevated in relation to the hypoxic and glycolytic phenotype of cancer through mechanisms previously discussed. Therefore, we expect the expression of these molecules to be decreased in animals treated with metabolic therapy and $HBO_2T$ compared to controls.

To gain a greater understanding of the mechanisms of the anti-cancer effects of these treatments, cell proliferation, viability, reactive oxygen species (ROS) production, and cell morphology of VM-M3 cells in vitro following exposure to low and high glucose, ketones, and $HBO_2T$ are measured. The rate of cell proliferation, cell viability, production, and membrane lipid peroxidation induced-changes in cell morphology (indicative of oxidative stress) of VM-M3/Fluc cells in response to treatment with low (3 mM) glucose, high (15 mM) glucose, 5 mM βHB, and $HBO_2T$ (100% $O_2$, 2.5 ATA) compared to control, non-treated cells. Cells are treated with low glucose (5 mM); high glucose (15 mM); 5 mM βHB; with/without hyperbaric oxygen therapy (100% $O_2$, 2.5 ATA).

VM-M3/Fluc cells are cultured in Eagle's Minimum Essential Medium with 2 mM L-glutamine, 10% fetal bovine serum, 1% penicillin-streptomycin, and 10 mM D-glucose. Cells will be maintained in a $CO_2$ incubator at 37° C. in 95% air and 5% $CO_2$. Cells receiving $HBO_2T$ are placed in a standard hyperbaric chamber and pressurized to 2.5 ATA absolute with 100% $O_2$ for 90 min. 5 mM HEPES is added to maintain $CO_2$ concentrations while in $HBO_2T$ chamber.

Cell proliferation rate is measured using the MTT Cell Proliferation Assay (ATCC). Cells are plated onto a 96 well plate and grown to desired density. Cells are treated for 72 hrs with low (5 mM) glucose, high (15 mM) glucose, or 5 mM βHB with or without $HBO_2T$ (100% $O_2$, 2.5 ATA absolute, for 90 min). In proliferating cells, MTT is reduced to purple formazan which absorbs light at 490-520 nm and whose excitation can be measured using standard fluorescent microscopy and spectrophotometry. Rapidly dividing cells reduce MTT at very high rates, indicating their rate of proliferation. Cell proliferation can also be measured with Ki67 immunohistochemistry staining, cell viability can also be evaluated with the LDH Cytotoxicity Assay (Cayman Chemical).

Cell viability is measured using the LIVE/DEAD Viability/Cytotoxicity Kit for Mammalian Cells (Invitrogen). Cells are grown to desired density on a coverslip and washed with Dulbecco's phosphate-buffered saline (D-PBS). Cells are treated for 72 hrs with low (5 mM) glucose, high (15 mM) glucose, or 5 mM βHB with or without $HBO_2T$ (100% $O_2$, 2.5 ATA absolute, for 90 min). The two-color fluorescence assay contains two probes which specifically label live or dead cells. Live cells possess ubiquitous intracellular esterases which cleave the non-fluorescent calcein AM into the highly fluorescent calcein. Calcein produces an intense green fluorescence with an excitation/emission of 495/515 nm. Ethidium homodimer-1 (Ethd-1) enters cells with damaged membranes and binds to nucleic acid. Ethd-1 bound to DNA produces a red fluorescence in dead cells with an excitation/emission of 495/635 nm. Live and dead cells are identified and quantified using standard fluorescent microscopy.

Presence of intracellular ROS is measured by detection of superoxide anion ($.O_2^-$) using 5 μM Dihydroethidium (DHE) following 72 hr treatment of low (5 mM) glucose, high (15 mM) glucose, or 5 mM βHB, with or without $HBO_2T$ (100% $O_2$, 2.5 ATA, 90 min.). DHE is permeable to the plasma membrane and freely enters the cell where it reacts with $.O_2^-$ to produce the oxidized ethidium. Ethidium intercalates into the DNA and fluoresces red with an excitation/emission of 485/515 nm which will be visualized using confocal fluorescent microscopy. Alternatively, ROS production can also be examined by the CellROX Deep Red Reagent (Invitrogen).

Atomic force microscopy (AFM) is utilized to analyze surface topography of VM-M3 cells in order to detect ultrastructural changes in cell morphology, such as lipid peroxidation-induced membrane blebbing (D'Agostino, et al. (2009) Acute hyperoxia increases lipid peroxidation and induces plasma membrane blebbing in human U87 glioblastoma cells. Neuroscience 159: 1011-1033; D'Agostino, et al. (2012) Development and testing of hyperbaric atomic force microscopy (AFM) and fluorescence microscopy for biological applications. Journal of microscopy 246: 129-142), following treatment with low (5 mM) glucose, high (15 mM) glucose, or 5 mM βHB. Hyperbaric atomic force microscopy (HAFM) will be similarly used to determine the effects of $HBO_2T$ (100% $O_2$, 2.5 ATA) on VM-M3 cell morphology.

$HBO_2T$ is known to increase ROS production in normal cells and to an even greater extent in cancer cells (Daruwalla & Christophi (2006) Hyperbaric oxygen therapy for malignancy: a review. World journal of surgery 30: 2112-2143). ROS cause oxidative stress, inducing lipid peroxidation-induced membrane blebbing which can be detected by AFM (D'Agostino, et al. (2009) Acute hyperoxia increases lipid peroxidation and induces plasma membrane blebbing in human U87 glioblastoma cells. Neuroscience 159: 1011-1033). As such VM-M3 cells should exhibit significant alterations in cell membrane morphology following $HBO_2T$. Ketones have been shown to reduce ROS production in healthy tissues (Maalouf, et al. (2007) Ketones inhibit mitochondrial production of reactive oxygen species production following glutamate excitotoxicity by increasing NADH oxidation. Neuroscience 145: 256-264), but it is unclear if they will attenuate ROS production to the same degree in cancer cells. Mitochondrial defects of cancer should limit the ability of βHB to inhibit ROS production lipid peroxidation in the VM-M3 cells. Since glucose restriction, ketone administration, and $HBO_2T$ have been shown to inhibit cancer progression, treatments should decrease proliferation rate and reduce viability in VM-M3 cells. Since metabolic therapy and $HBO_2T$ work by overlapping mechanisms, the anti-cancer effects of low glucose and βHB treatment should be enhanced by $HBO_2T$.

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between. Now that the invention has been described, What is claimed is:

What is claimed is:

1. A method of reducing metastasis in cancer, comprising: administering to an animal with a metastatic cancer a therapeutically effective amount of acetoacetate, 1,3-butanediol acetoacetate monoester, 1,3-butanediol acetoacetate diester, R,S-1,3-butanediol-diacetoacetate ester, R-1,3-butanediol diacetoacetate ester, or a combination thereof.

2. The method of claim 1, further comprising subjecting the animal to a hyperbaric, oxygen-enriched environment.

3. The method of claim 2, wherein the hyperbaric, oxygen-enriched environment is 100% oxygen.

4. The method of claim 3, wherein the hyperbaric, oxygen-enriched environment is at 2.5 ATA absolute.

5. The method of claim 3, wherein the animal is subjected to the hyperbaric, oxygen-enriched environment for 90 minutes three times a week.

6. The method of claim 1, wherein the acetoacetate, 1,3-butanediol acetoacetate monoester, 1,3-butanediol acetoacetate diester, R,S-1,3-butanediol-diacetoacetate ester, R-1,3-butanediol diacetoacetate ester, or a combination thereof is administered at 10 g/kg of body weight.

* * * * *

UNITED STATES PATENT AND TRADEMARK OFFICE
CERTIFICATE OF CORRECTION

PATENT NO. : 9,801,903 B2
APPLICATION NO. : 14/698136
DATED : October 31, 2017
INVENTOR(S) : Dominic Paul D'Agostino et al.

Page 1 of 1

It is certified that error appears in the above-identified patent and that said Letters Patent is hereby corrected as shown below:

In the Specification

Column 1, Line 14 insert:
--STATEMENT OF GOVERNMENT INTEREST
This invention was made with government support N00014-09-1-0244 awarded by the Office of Naval Research. The Government has certain rights in the invention.--

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*